(12) United States Patent
Mozayeny

(10) Patent No.: US 12,397,112 B2
(45) Date of Patent: Aug. 26, 2025

(54) SMART POWER STRIP

(71) Applicant: Koorosh Mozayeny, Newport Beach, CA (US)

(72) Inventor: Koorosh Mozayeny, Newport Beach, CA (US)

( * ) Notice: Subject to any disclaimer, the term of this patent is extended or adjusted under 35 U.S.C. 154(b) by 0 days.

(21) Appl. No.: 18/421,331

(22) Filed: Jan. 24, 2024

(65) Prior Publication Data

US 2024/0238517 A1 Jul. 18, 2024

Related U.S. Application Data

(63) Continuation of application No. 18/379,444, filed on Oct. 12, 2023, which is a continuation of application No. 18/214,812, filed on Jun. 27, 2023, now abandoned, which is a continuation of application No. 18/121,955, filed on Mar. 15, 2023, now abandoned, which is a continuation of application No. 17/990,499, filed on Nov. 18, 2022, now abandoned, which is a continuation of application No. 17/885,956, filed on Aug. 11, 2022, now abandoned, which is a continuation of application No. 17/744,102, filed on May 13, 2022, now abandoned, which is a continuation of application No.
(Continued)

(51) Int. Cl.
| | |
|---|---|
| *A61M 5/172* | (2006.01) |
| *G06F 1/26* | (2006.01) |
| *H01R 25/00* | (2006.01) |
| *H02J 3/00* | (2006.01) |

(52) U.S. Cl.
CPC ............ *A61M 5/1723* (2013.01); *G06F 1/26* (2013.01); *H02J 3/00* (2013.01); *A61M 2230/201* (2013.01); *H01R 25/003* (2013.01)

(58) Field of Classification Search
CPC . A61M 5/1723; A61M 2230/201; G06F 1/26; H02J 3/00; H01R 25/003; Y02B 70/3225; Y04S 20/222
See application file for complete search history.

(56) References Cited

U.S. PATENT DOCUMENTS

| | | |
|---|---|---|
| 5,229,937 A | 7/1993 | Evelyn-Veere |
| 5,598,349 A | 1/1997 | Elliason et al. |
(Continued)

FOREIGN PATENT DOCUMENTS

WO   WO 2011/109303   9/2011

OTHER PUBLICATIONS

International Preliminary Report on Patentability, re PCT Application No. PCT/US2011/026506, issued Sep. 4, 2012, mailed Sep. 13, 2012.
(Continued)

*Primary Examiner* — Ziaul Karim
(74) *Attorney, Agent, or Firm* — Knobbe, Martens, Olson & Bear, LLP

(57) ABSTRACT

A power strip includes a controller that controls the transfer of electricity to one or more outlet electrical connectors based at least in part on a set of rules and certain status information. Some embodiments provide for apparatuses and methods of controlling the transfer of electricity to one or more outlet electrical connectors of a power strip based on various status information, such as cost, personal preferences, time information, power consumption.

20 Claims, 18 Drawing Sheets

Related U.S. Application Data

17/667,276, filed on Feb. 8, 2022, now abandoned, which is a continuation of application No. 17/547,910, filed on Dec. 10, 2021, now abandoned, which is a continuation of application No. 17/385,658, filed on Jul. 26, 2021, now abandoned, which is a continuation of application No. 17/320,749, filed on May 14, 2021, now abandoned, which is a continuation of application No. 17/174,129, filed on Feb. 11, 2021, now abandoned, which is a continuation of application No. 17/072,712, filed on Oct. 16, 2020, now abandoned, which is a continuation of application No. 16/893,144, filed on Jun. 4, 2020, now abandoned, which is a continuation of application No. 16/712,657, filed on Dec. 12, 2019, now abandoned, which is a continuation of application No. 16/529,130, filed on Aug. 1, 2019, now abandoned, which is a continuation of application No. 15/903,932, filed on Feb. 23, 2018, now abandoned, which is a continuation of application No. 14/946,479, filed on Nov. 19, 2015, now abandoned, which is a continuation of application No. 13/768,824, filed on Feb. 15, 2013, now abandoned, which is a continuation of application No. 13/037,095, filed on Feb. 28, 2011, now abandoned.

(60) Provisional application No. 61/309,363, filed on Mar. 1, 2010.

(56) References Cited

U.S. PATENT DOCUMENTS

| | | | |
|---|---|---|---|
| 5,644,173 A | 7/1997 | Elliason et al. | |
| 5,696,695 A | 12/1997 | Ehlers et al. | |
| 6,121,695 A * | 9/2000 | Loh | H02J 9/062 |
| | | | 307/64 |
| 6,311,105 B1 | 10/2001 | Budike, Jr. | |
| 6,735,705 B1 | 5/2004 | Egbert et al. | |
| 6,894,254 B2 * | 5/2005 | Hauschulz | G05D 23/1935 |
| | | | 219/486 |
| 7,062,361 B1 | 6/2006 | Lane | |
| 7,274,303 B2 * | 9/2007 | Dresti | G08C 19/28 |
| | | | 398/115 |
| 7,349,766 B2 | 3/2008 | Rodgers | |
| 7,516,343 B2 * | 4/2009 | Bhogal | G06F 1/3203 |
| | | | 713/320 |
| 7,541,941 B2 | 6/2009 | Bogolea et al. | |
| 7,606,639 B2 | 10/2009 | Miyaji | |
| 7,622,822 B2 * | 11/2009 | Gelonese | G06F 1/3203 |
| | | | 307/38 |
| 7,705,484 B2 * | 4/2010 | Horst | H02J 3/14 |
| | | | 307/35 |
| 7,738,999 B2 * | 6/2010 | Petite | H02J 13/00034 |
| | | | 700/286 |
| 7,844,370 B2 | 11/2010 | Pollack et al. | |
| 7,956,492 B2 * | 6/2011 | Lee | H01R 13/7038 |
| | | | 307/115 |
| 7,994,654 B2 * | 8/2011 | Lee | G06F 1/266 |
| | | | 307/39 |
| 8,093,750 B2 * | 1/2012 | Ko | G06F 1/266 |
| | | | 307/38 |
| 8,094,034 B2 * | 1/2012 | Patel | G06F 17/00 |
| | | | 340/657 |
| 8,174,149 B2 * | 5/2012 | Chapel | H01R 13/6683 |
| | | | 307/64 |
| 8,213,144 B2 * | 7/2012 | Papallo | H02J 13/00007 |
| | | | 361/63 |
| 8,229,602 B2 * | 7/2012 | Montgomery | H02J 3/14 |
| | | | 700/291 |
| 8,260,471 B2 * | 9/2012 | Storch | H02J 3/14 |
| | | | 700/297 |
| 8,271,815 B2 * | 9/2012 | Lin | G06F 1/266 |
| | | | 713/340 |
| 9,703,349 B2 * | 7/2017 | Gelonese | G06F 1/32 |
| 2005/0286184 A1 * | 12/2005 | Campolo | H01R 25/003 |
| | | | 361/42 |
| 2006/0267574 A1 | 11/2006 | Howard | |
| 2007/0078314 A1 | 4/2007 | Grounsell et al. | |
| 2008/0039980 A1 * | 2/2008 | Pollack | B60L 53/68 |
| | | | 700/295 |
| 2008/0114299 A1 | 5/2008 | Damgaard-Sorensen et al. | |
| 2008/0194924 A1 * | 8/2008 | Valk | A61B 5/4839 |
| | | | 604/890.1 |
| 2008/0252141 A1 * | 10/2008 | Horst | H02J 3/14 |
| | | | 307/35 |
| 2008/0272934 A1 | 11/2008 | Wang et al. | |
| 2008/0281473 A1 | 11/2008 | Pitt | |
| 2009/0045803 A1 * | 2/2009 | Schoettle | G01R 21/133 |
| | | | 324/140 D |
| 2009/0230950 A1 * | 9/2009 | Czarnecki | G01R 1/0408 |
| | | | 324/142 |
| 2010/0094475 A1 | 4/2010 | Masters et al. | |
| 2010/0268562 A1 | 10/2010 | Anderson | |
| 2010/0271802 A1 | 10/2010 | Recker et al. | |
| 2011/0209765 A1 | 9/2011 | Mozayeny | |
| 2011/0213332 A1 | 9/2011 | Mozayeny | |
| 2011/0213510 A1 * | 9/2011 | Mozayeny | G06F 1/26 |
| | | | 700/297 |
| 2012/0060044 A1 * | 3/2012 | Jonsson | H01R 13/6683 |
| | | | 713/340 |
| 2013/0261834 A1 | 10/2013 | Mozayeny | |
| 2014/0088779 A1 * | 3/2014 | Chen | G06F 1/266 |
| | | | 700/295 |
| 2014/0180490 A1 | 6/2014 | Mozayeny | |
| 2014/0312691 A1 * | 10/2014 | Doljack | H02J 7/0036 |
| | | | 307/29 |
| 2016/0156187 A1 | 6/2016 | Mozayeny | |
| 2018/0316189 A1 | 11/2018 | Mozayeny | |
| 2019/0109723 A1 * | 4/2019 | Ebrom | H05B 6/688 |
| 2022/0379027 A1 | 12/2022 | Mozayeny | |
| 2024/0238517 A1 * | 7/2024 | Mozayeny | A61M 5/1723 |

OTHER PUBLICATIONS

International Search Report and Written Opinion, re PCT Application No. PCT/US2011/026506, mailed Nov. 15, 2011.

* cited by examiner

SMART POWER STRIP

RELATED APPLICATIONS

This application is a continuation of continuation of U.S. patent application Ser. No. 18/379,444, filed on Oct. 12, 2023, which is a continuation of U.S. patent application Ser. No. 18/214,812, filed on Jun. 27, 2023, which is a continuation of U.S. patent application Ser. No. 18/121,955, filed on Mar. 15, 2023, which is a continuation of U.S. patent application Ser. No. 17/990,499, filed on Nov. 18, 2022, which is a continuation of U.S. patent application Ser. No. 17/885,956, filed on Aug. 11, 2022, which is a continuation of U.S. patent application Ser. No. 17/744,102, filed on May 13, 2022, which is a continuation of U.S. patent application Ser. No. 17/667,276, filed on Feb. 8, 2022, which is a continuation of U.S. patent application Ser. No. 17/547,910, filed on Dec. 10, 2021, which is a continuation of U.S. patent application Ser. No. 17/385,658, filed on Jul. 26, 2021, which is a continuation of U.S. patent application Ser. No. 17/320,749, filed on May 14, 2021, which is a continuation of U.S. patent application Ser. No. 17/174,129, filed on Feb. 11, 2021, which is a continuation of U.S. patent application Ser. No. 17/072,712, filed on Oct. 16, 2020, which is a continuation of U.S. patent application Ser. No. 16/893,144, filed on Jun. 4, 2020, which is a continuation of U.S. patent application Ser. No. 16/712,657, filed on Dec. 12, 2019, which is a continuation of U.S. patent application Ser. No. 16/529,130, filed on Aug. 1, 2019, which is a continuation of U.S. patent application Ser. No. 15/903,932, filed on Feb. 23, 2018, which is a continuation of U.S. patent application Ser. No. 14/946,479, filed on Nov. 19, 2015, which is a continuation of U.S. patent application Ser. No. 13/768,824, filed on Feb. 15, 2013, which is a continuation of U.S. patent application Ser. No. 13/037,095, filed on Feb. 28, 2011, which claims the benefit of the of U.S. Provisional Application No. 61/309,363, filed on Mar. 1, 2010, the entirety of each of which is incorporated herein by reference.

BACKGROUND

Field

The present disclosure relates generally to smart power strips.

Description of the Related Art

Power strips are commonly employed for powering electronic appliances, including computer systems, high fidelity and stereo equipment, home theatre installations and the like. Current sensing devices are known in the art for controlling the power supplied by one or more secondary electrical outlets of a power strip. However, power strips have not previously had the capability of controlling the power supplied to secondary outlets based on a set of rules.

SUMMARY

Embodiments described herein have several features, no single one of which is solely responsible for their desirable attributes. Without limiting the scope of the inventions as expressed by the claims, some of the advantageous features will now be discussed briefly.

Some embodiments provide a power strip comprising a first inlet electrical connector configured to be plugged into a first electrical socket and to receive an input of electricity from the first electrical socket, one or more outlet electrical connectors electrically coupled to the first inlet electrical connector and configured to receive a second inlet electrical connector of an energy consuming device for transmission of at least a portion of the electricity from the first inlet electrical connector to the energy consuming device, and a controller configured to control the transfer of electricity from the first inlet electrical connector to the one or more outlet electrical connectors based at least in part on a set of rules and status information related to the set of rules.

The status information can include electricity rate information, information related to personal preferences of a user, energy demands of the energy consuming device, time of day and/or day of week information, information received from a smart grid electrical system, or other information.

The controller can be further configured to receive information from a smart meter and to control the input of electricity to the one or more outlet electrical connectors based on the information. The controller can be further configured to receive feedback information from the energy consuming device and to control the input of electricity to the one or more outlet electrical connectors based on the feedback information. The controller may be programmable by a user.

Some embodiments provide a method of regulating the distribution of electrical energy comprising providing a power strip comprising a first inlet electrical connector configured to be plugged into a first electrical socket and to receive an input of electricity from the first electrical socket, and one or more outlet electrical connectors electrically coupled to the first inlet electrical connector and configured to receive a second inlet electrical connector of an energy consuming device for transmission of at least a portion of the electricity from the first inlet electrical connector to the energy consuming device, and controlling the transfer of electricity from the first inlet electrical connector to the one or more outlet electrical connectors based at least in part on a set of rules and status information related to the set of rules.

For purposes of this summary, certain aspects, advantages, and novel features of the invention are described herein. It is to be understood that not necessarily all such aspects, advantages, and features may be employed and/or achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes, and should in no way be interpreted as limiting the scope of the inventive subject matter. In addition, various features of different disclosed embodiments can be combined to form additional embodiments, which are part of this disclosure.

DETAILED DESCRIPTION OF THE PREFERRED EMBODIMENTS

Figure 1:
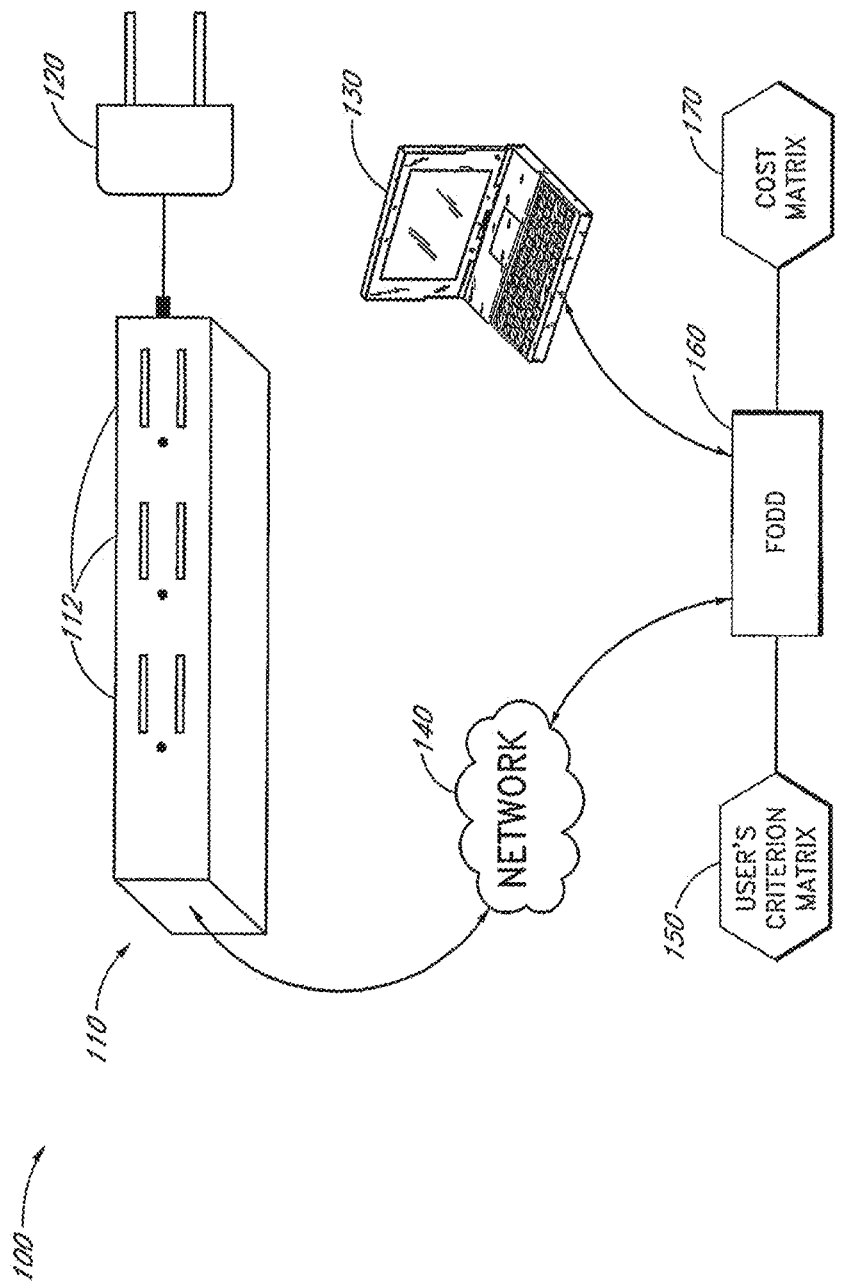
FIG. 1 illustrates an embodiment of a smart power strip.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent.

Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Flow Optimizer Decision Device (FODD)

A Flow Optimizer Decision Device (FODD) may be a hardware device. The device may use one or more algorithms to calculate and make complex decisions on how to distribute one-directional or bi-directional flows in a grid. Regulation of flow using a hardware device may provide certain advantages relating to the ability to make decisions in a limited time frame or even in real-time. Moreover, calculations relating to the regulation or optimization of flow may become significantly more intricate in connection with complex criterion matrices. These, as well as other considerations indicate the desirability of a dedicated hardware device for regulating flow. Such devices often communicate with one or more sensors (e.g., remote sensors) and make decisions in real-time. FODD is such a device.

Embodiments in which a FODD is a dedicated hardware device may provide a number of benefits, such as facilitating increased system security. For example, a dedicated hardware device may be a component of a proprietary system. Proprietary systems may be more difficult for hackers or other persons or systems to infiltrate. Such security may provided added protection of privacy, resources, system integrity, etc.

In certain embodiments, a hardware device may be required for proper function of the FODD. For example, in a medical environment, a FODD may be implanted in a patient. In water or electricity distribution system environments, utilities may have their own interface with which a FODD may communicate. With further reference to water distribution, in an exemplary home sprinkler system, it may be impractical, or expensive to run a FODD system as software on a separate computer system, and therefore a dedicated FODD device may be desired.

A FODD may be suitable in applications that require controlling flow (e.g., of physical matter, resources, goods, supply chains, energy, data, etc.) based on criteria represented in or by static or dynamic criterion matrices. As is apparent with respect to the exemplary flow charts in FIGS. 9-12, a FODD can use one or more criterion matrices to regulate the distribution of the flow of a relevant parameter. Criterion in a criterion matrix may include, relate to, or be based on certain status information relating to the particular system of which the FODD is a part. A FODD may be a bi-directional device that is capable of handling positive as well as negative flows. In certain embodiments, bi-directional flow regulation may be achieved through the use of separate negative and positive flow criterion matrices. A FODD may operate in connection with a criterion matrix that is configured to be automatically modified in accordance with preferences "learned" by the system, i.e., the FODD may be configured to adapt to accommodate or reflect certain perceived preferences, behaviors, conditions, etc.

The application of FODD devices in various fields is vast; however, to demonstrate the devices' use, embodiments are disclosed herein in the context of the following exemplary fields: 1) Distribution of electrical power, such as in connection with the new Smart Grid Electrical system, 2) distribution of water, such as in irrigation systems, 3) delivery of medication to a patient, and 4) distribution of economic resources, e.g., vis-à-vis cash flow between and among business partners ("Partner Cash Flow Analysis").

Electrical Grid System

In certain embodiments, a FODD may be used to optimize and coordinate the flow of electrical energy within an electrical system. For example, implementation of a FODD may be desirable for distributing electrical flow in the new smart grid system being implemented in various municipalities throughout the world. While certain currently implemented flow regulation systems involve one-way manual flow distribution, certain systems incorporating a FODD may implement a two-way communication flow system. Smart grid is used to control the delivery of electricity to end users or customers by monitoring and controlling the end user's appliances. Countries such as France, England, China, and US are moving rapidly to this new system.

Therefore, the electrical industry is being transformed from a centralized producer-controlled network to one that is less centralized. This two-way flow of electricity and information will be capable of monitoring everything from power plants to customer preferences to individual appliances.

Many countries are adopting the smart grid system. Please note the following examples:

Canada

The government of Ontario, Canada, through the Energy Conservation Responsibility Act in 2006, has mandated the installation of Smart Meters in all Ontario businesses and households by 2010.

China

On May 21, 2009, China has announced an aggressive framework for Smart Grid deployment. As part of its current 5-year plan, China is building a Wide Area Monitoring system (WAMS) and by 2012 plans to have PMU sensors at all generators of 300 megawatts and above, and all substations of 500 kilovolts and above.

European Union

Development of smart grid technologies is part of the European Technology Platform (ETP) initiative and is called the Smart Grids Technology platform. The Smart Grids European Technology Platform for Electricity Networks of the Future began its work in 2005. Its aim is to formulate and promote a vision for the development of European electricity networks looking towards 2020 and beyond United States Support for smart grids became federal policy with passage of the Energy Independence and Security Act of 2007. The law, Title13, sets out $100 million in funding per fiscal year from 2008-2012, establishes a matching program to states, utilities and consumers to build smart grid capabilities, and creates a Grid Modernization Commission to assess the benefits of demand response and to recommend needed protocol standards. The Energy Independence and Security Act of 2007 directs the National Institute of Standards and Technology to coordinate the development of smart grid standards, which FERC would then promulgate through official rulemakings.

Electricity Distribution System

In certain embodiments, a Flow Optimizer Decision Device (FODD) algorithm and computer model can be used to: a) control and optimize the use of various user's appliances in light of cost matrices and user criterion requirements, among other possible uses b) help generate cost matrices to be used to set utility prices, and c). control and optimize the flow of electricity between various power stations, homes, offices, factories, etc.

A. Control and Optimization of Use of Various User Appliances in Light of Cost Matrices and Users Criterion Requirements In certain embodiments, a cost matrix (cost to the user) is calculated and transmitted to an end user. In certain embodiments, this information, together with the new smart meters being implemented, may help determine the cost of energy to the end user at a given time.

As discussed in further detail below, the user, like a utility company, for example, may have its own criterion matrix. The user criterion matrix may include information relating to various parameters and/or user preferences. In certain embodiments, the parameters and/or preferences are manually input by a user. This could be done in several ways, including, for example, through the use of a computer questionnaire or form. This matrix would describe the user's preferences.

For example, a user may not like to run the pool heater if the cost of electricity reaches a certain amount. This information may be inside the user's preference/criterion matrix. In certain embodiments, the parameters and/or preferences are set automatically. For example, parameters or preferences may be learned by the system based on the electricity usage practices of the user. The FODD may act as a form of "artificial intelligence," wherein parameters or preferences are set or modified without required user input. This may be beneficial in scenarios where a user/consumer has inadequate time or desire to modify or otherwise input information relating to parameters or preferences. The following example may help explain the attributes of such an embodiment: a homeowner returns home from work in the evening and therefore does not use the home's water supply during the day. A FODD-based water heating system therefore may "learn" that there is no need to maintain water temperature levels during the middle of the day. The Flow Optimizer Decision Device (FODD) may use the user's criterion matrix to make decisions on which appliance(s) to turn on or off in light of the current cost matrix transmitted by the utility companies. In certain embodiments, the FODD makes decisions relating to the distribution of electrical energy based on a user end criterion matrix, without input from an electricity provider. The FODD can be configured to make decisions in real-time.

It may be beneficial to implement a FODD in connection with smart appliances, which may be configured to access a smart grid, as discussed above, and operate accordingly. However, not all appliances currently in use are smart appliances. Use of "Smart-Grid" technology and associated variable power rate structure might have required a user to obtain a new set of "smart" appliances. However, users of legacy devices may not want to discard existing, non-"smart," appliances. A "Smart Power Strip" may provide the option to appliance users to maintain use of legacy devices and still take advantage of smart grid technology. In certain embodiments, if a user plugs his or her legacy devices into a smart power strip, the devices may be able to take on "smart" attributes. In certain embodiments, a device may be hard-wired to a FODD unit, such as SPS 110.

The Smart Power Strip (SPS) is an electrical power strip configured to allow for the regulation of power to its outlet(s) according to control logic. FIG. 1 provides an illustration of an embodiment of an energy management system incorporating an SPS 110. The SPS is associated with a FODD 160, which may be incorporated into the power strip 110 itself, or may be an independent device in communication with the power strip. Discussion of SPS 110 herein may refer to either a power strip separate from, but in communication with, a FODD, or to a power strip with a built in FODD. The SPS 110 includes an inlet electrical connector 120, such as an electrical plug that connects to a power source, such as via a wall electrical outlet. The SPS 110 includes one or more outlet electrical connectors 112 for allowing electrical connection of devices, such as conventional, non-smart, appliances. In certain embodiments, one or more of the electrical connectors 112 is controllable independently of one or more other electrical connectors 112. FIG. 1 further depicts a user's criterion matrix 150 and a cost matrix 170, which concepts are discussed above with reference to FIGS. 4 and 5. In certain embodiments, the SPS 110 operates or behaves in accordance with either the cost matrix 170, the user's criterion matrix 150, or both.

In certain embodiments, the SPS 110, or its associated FODD 160, is programmable. The SPS may be programmed, for example, via a monitoring and/or programming station 130, such as a user input device (shown as a personal computer in FIG. 1). Communication between the SPS 110, or FODD 160, may include two-way communication, or may be limited to flow of information in one direction. In certain embodiments, the SPS 110, or FODD 160, is programmable through the internet, and programming may be performed wirelessly, or using a hardwire connection. For example, the SPS 110 may work with the new Smart Metering and/or a FODD 160 unit to power down or power up various appliances connected to it. For example, if a utility cost increases to a certain threshold level, the SPS may power down one or more appliances, e.g., non-critical appliances, but may keep power turned on to a one or more other devices, e.g., critical devices, such as a needed medical equipment.

In certain embodiments, an SPS 110 may operate in accordance with the FODD algorithm illustrated in FIGS. 9-12 (discussed below). However, an SPS 110 may, in certain embodiments operate in accordance with any other suitable flow-regulation algorithm. Furthermore, the system 100 may include an independent FODD device 160, which communicates with the SPS 110, or may include an integrated FODD algorithm built into the SPS 110. In certain embodiments, the power strip may be programmed to turn on or off at certain times or for certain time intervals. In embodiments including an independent FODD that communicates with the SPS 110, such communication may be achieved via a wired or wireless connection 140, such as a local area network, an internet connection, or any other suitable connection.

The SPS 110 may obtain feedback information from one or more devices that are electrically connected to the SPS 110, and such information may be relied upon by the FODD 160 or SPS 110 in determining how to regulate electrical power. Feedback information may be obtained by the SPS 110 in addition to, or in place of, information obtained from a smart meter, independent or integrated FODD, etc. For example, a cell phone may be connected to the SPS 110, such that the cell phone provides information related to its charge state, or other criteria, for consideration by the SPS 110. Consider, for example, the following rules, or criteria that may be provided by the cell phone to the SPS: if the cell phone is less than 70% charged, charge it no matter what the cost; if the cell phone is at least 70% charged, and the energy cost is less than a threshold amount, resume charging until the cell phone reaches 90%, and so on. The advantages associated with the use of an SPS may be more apparent in the context of more power-hungry devices, such as electric automobiles.

Figure 2:
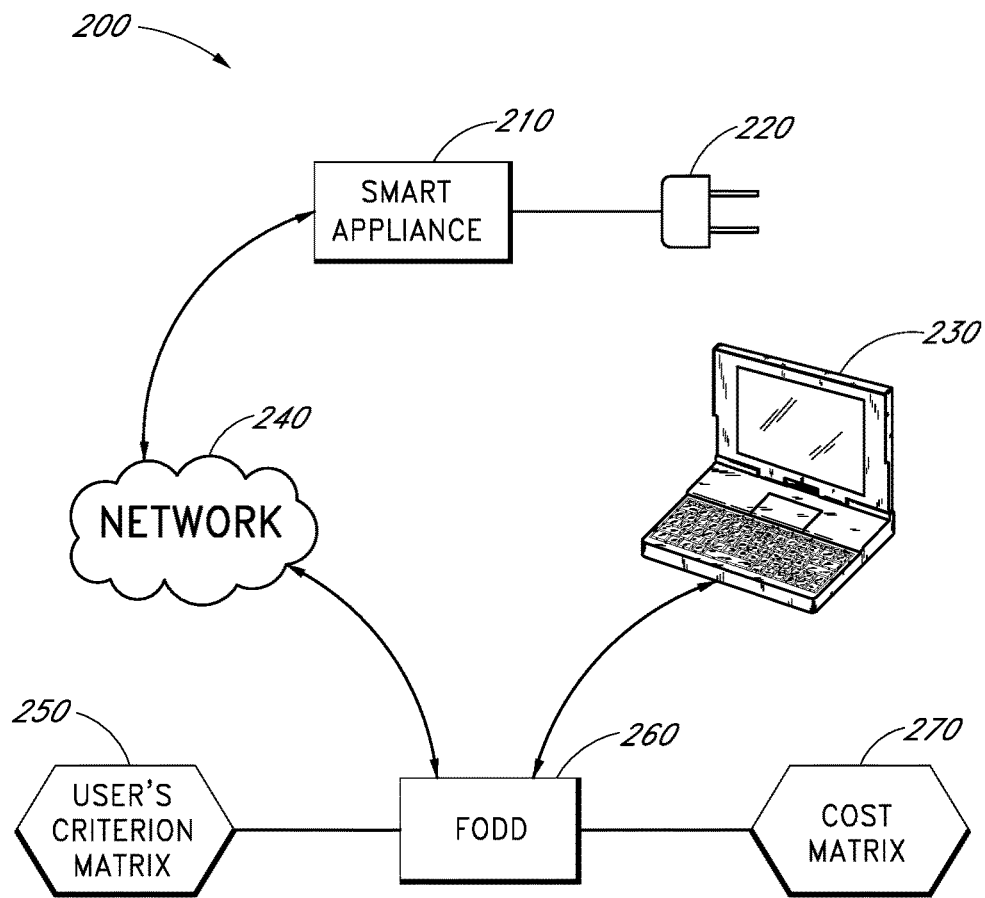
FIG. 2 illustrates an embodiment of a energy management system.

Much of the discussion above, with respect to FIG. 1, of system 100 is applicable to the system 200 of FIG. 2. FIG. 2 illustrates an energy management system generally incorporating a smart appliance 210, one example of which would be a smart power strip, as discussed above. Other examples of smart appliances that may be suitable for system 200 include smart washing machines, dishwashers, climate control devices, television or other media devices, etc.

Figure 3:
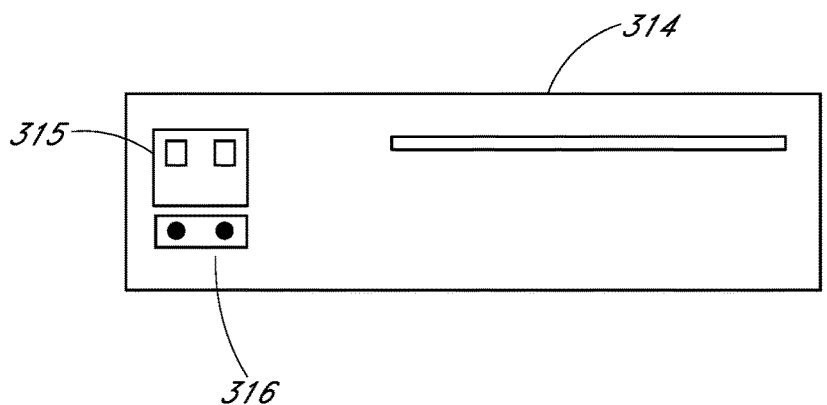
FIG. 3 illustrates an embodiment of a meter for a smart appliance.

FIG. 3 illustrates an embodiment of a meter and/or control component for a smart appliance or smart power strip. In certain embodiments, the component 314 includes a clock 315. In certain embodiments, the clock and controls 315 can be set by a FODD using a user's utility matrix and/or cost matrix with a manual override. In certain embodiments, the clock and/or controls can be set using controls on the smart appliance or power strip. The meter may include one or more indicators 316 indicating the cost of relevant electricity consumption, or any other flow-related parameter. Any indication means may be employed to communicate cost information to a user. For example, a green or blue light or color may indicate low cost; a yellow or orange light or color may indicate moderate cost; and a red light or color may indicate a high cost. Cost information for the meter may be provided by the FODD, user's matrix or cost matrix. In certain embodiments, a meter and/or control component includes a sophisticated display. In certain embodiments, information associated with a FODD may be accessed through a web interface. For example, a system may be configured such that a user could obtain information as to cost, etc., through a web interface.

B. Control and Optimization of Flow of Electricity Between Various Power Stations, Homes, Offices, Factories, Etc.

Figure 4:
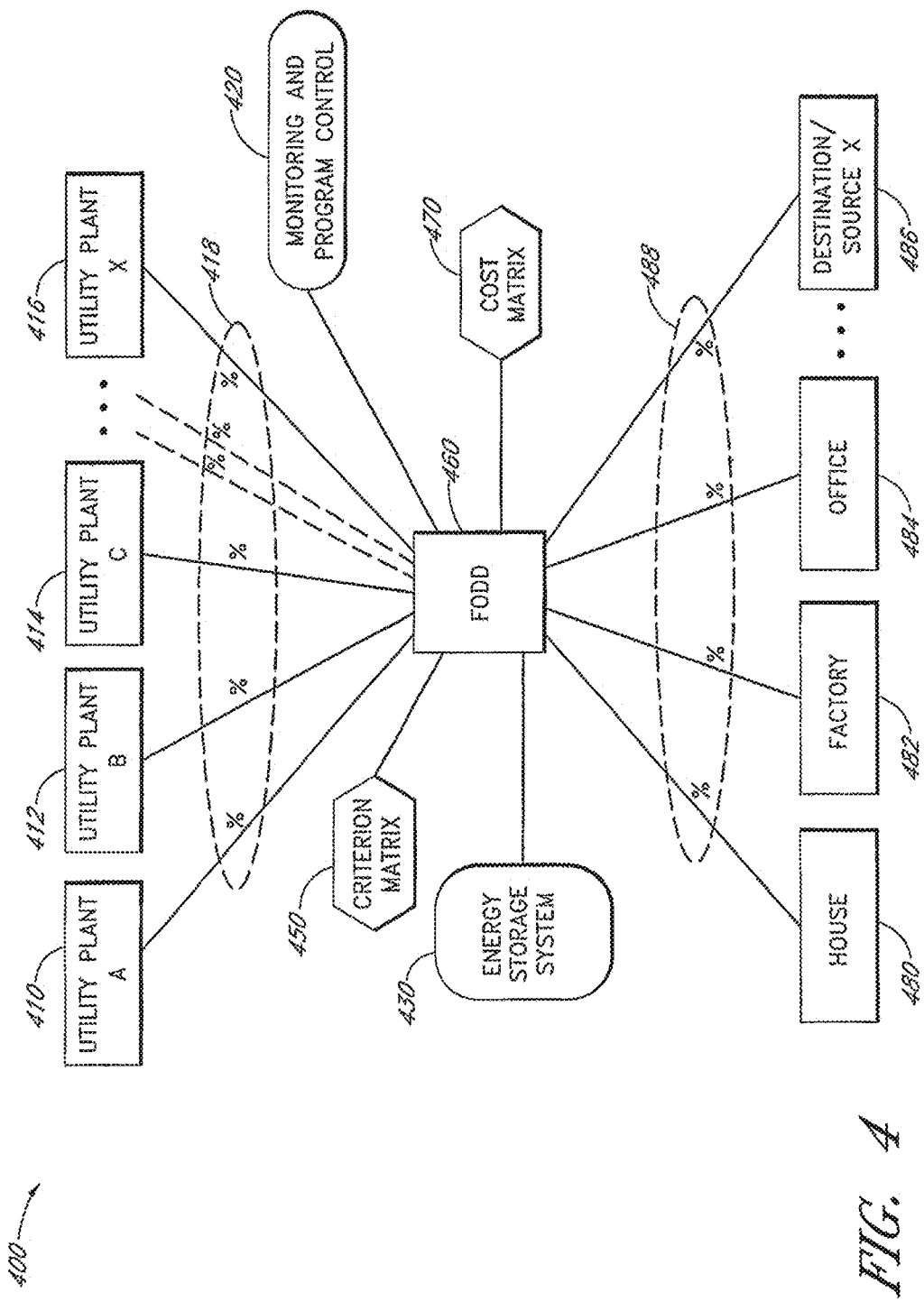
FIG. 4 illustrates an embodiment of an electrical flow regulation system.

FIG. 4 depicts an embodiment of an electrical flow regulation system which demonstrates the control and optimization of the flow of electricity between various power stations, homes, offices, and/or factories, etc. The various utility plants depicted in FIG. 4 may generate electricity from various sources. For example, Utility Plan A 410 may generate electricity from a fossil fuel, such as coal, or through another means of electricity generation (e.g., nuclear reaction), while Utility Plant B 412 may generate electricity from a renewable source (e.g., wind, hydropower, solar energy, biomass, biofuel, geothermal energy, etc.). An embodiment in accordance with FIG. 4 may include a complex criterion matrix 450 with certain requirements or rules, such as, for example: i) Utility Plant A 410 should run at least at 10% of maximum capacity, ii) all available energy beyond 10% of Utility Plant A's 410 maximum capacity should be provided by Utility Plant B 412 (renewable), until Utility Plant B 412 is running at 70% of maximum capacity, iii) once Utility Plant B reaches 70% maximum capacity, then power should be drawn equally from Utility Plant A 410 and B 412 equally until Utility Plant B 412 reaches 85% capacity.

As can be seen, the above criterion requirements can become very complex, especially in the context of numerous power generation facilities. Moreover, an end user, such as a home, may also generate electricity from one or more renewable sources, which may be considered as another "power plant" in the framework of FIG. 4.

The criterion requirements detailed above may be downloaded to the Flow Optimizer Decision Device 460 (FODD), or otherwise incorporated into the FODD 460. The device may then determine how much energy to draw from each power plant based on the above criterion matrix, and/or other factors, such as the current demand for energy.

As illustrated in FIG. 4, the collective input 418 (and/or output in the case of bi-directional flow) of electrical energy in the system 400 may be provided to the FODD 460 for consideration in determining distribution of the electrical energy. As indicated in FIG. 4, each source of energy provides some portion, or percentage, of the overall input 418 of electrical power. The percentage of electrical power drawn from a given energy source may be determined by the FODD 460 based on a criterion matrix 450 and/or one or more parameters, and may be positive or negative. In certain embodiments, determinations by the FODD 460 take into account parameters such as cost, whether or not the source is a renewable source, distance, regulatory requirements, or other relevant factors. Decisions relating to the distribution of energy from one or more of the energy sources 410-416 may be made automatically. In certain embodiments, decisions are made manually in connection with suggestions generated by the FODD. Furthermore, the FODD 460 may make decisions according to any desired time increment (e.g., seconds, minutes, etc.), or in real time, or substantially real time.

The collective distribution 488 of energy too and/or from energy consumption/production modules 480-486 is also depicted. In certain embodiments, modules 480-486 in FIG. 4 represent end users, or points of consumption of energy provided by one or more electrical power generators 410-416. However, as discussed above, systems in accordance with embodiments disclosed herein may be bi-directional. In such systems, modules 480-486 may be equipped to generate or otherwise contribute electrical power back to the grid. For example, a home, which in certain embodiments acts as an energy consumer, may be equipped with solar panels that generate electrical energy from the Sun. Electrical energy produced by the home in excess of its needs may be provided to the system for distribution.

C. Generation of Cost Matrices to be Used to Set Utility Prices

The Flow Optimizer Decision Device may calculate the percentage distribution of energy draw from each source. In certain embodiments, this information, or any other desired parameter, is used to generate the cost of the energy at a given time, which information may be contained in a cost matrix 470. Such a cost matrix 470 may include price structure for various user classifications. In certain embodiments, the FODD 460 operates in accordance with the cost matrix 470 or a user's criterion matrix 450, or both. Moreover, the cost/price structure may fluctuate in real-time as percentage distribution from each source changes.

Figure 5:
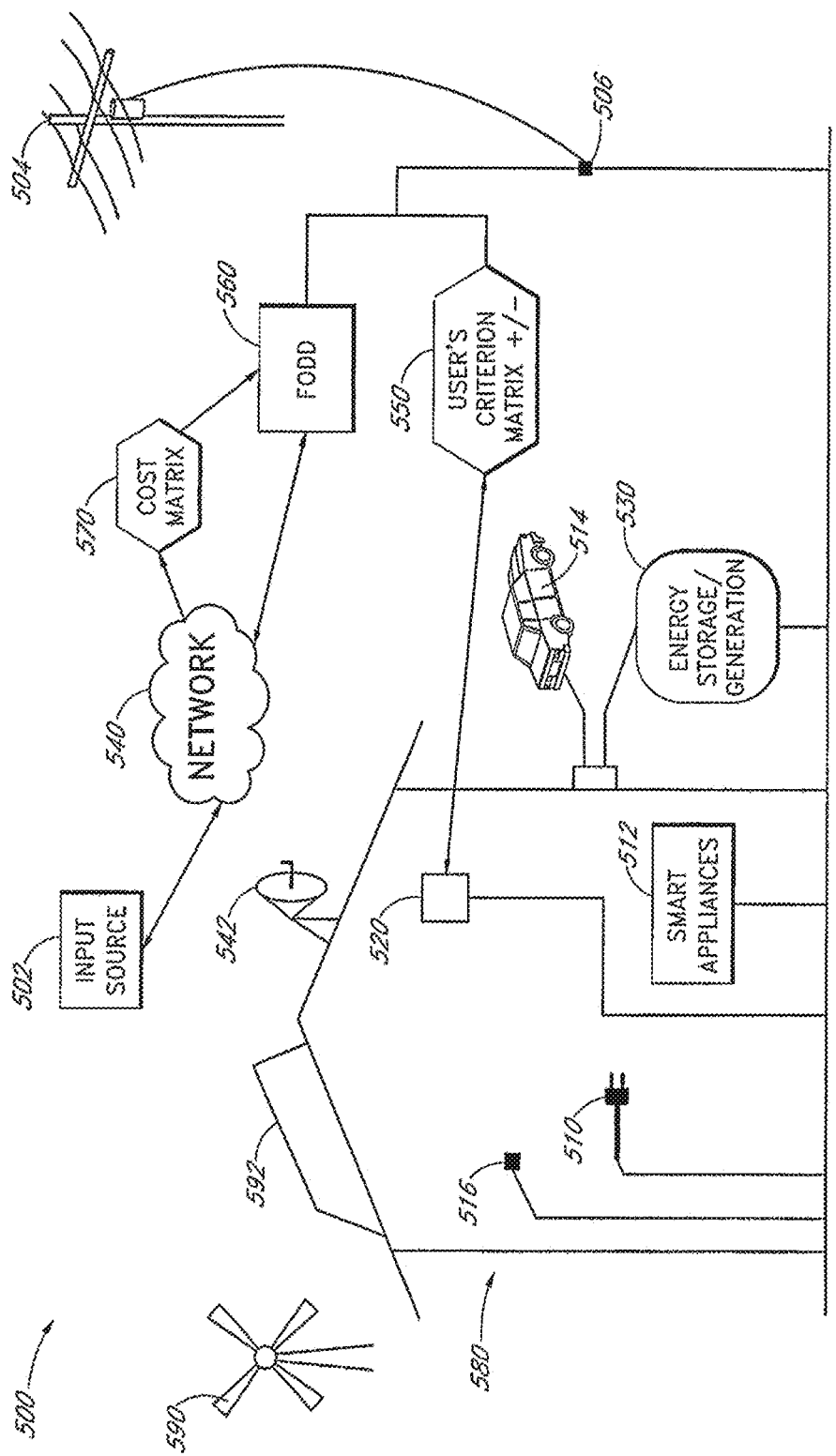
FIG. 5 illustrates an embodiment of an electrical flow regulation system.

FIG. 5 depicts the user end of an embodiment of an electrical flow regulation system. In the illustrated embodiment, a FODD 560 manages the flow of electrical power between an end user home 580 and a utility source 504. In certain embodiments, the FODD 560 is configured to handle negative, as well as positive, flows of electricity. The system 500 may include a cost matrix 570 as well as a user's criterion matrix 550. The FODD 560 and/or the cost matrix 570 may receive information input from a utility company, or other source of information 502. The transfer of information between the input source 502 and the FODD 560 and/or cost matrix 570 may be either a one or two-way form of communication. For example, information relating to the electricity consumption of an end user (e.g., home 580) may be communicated to the source 502. In addition, communication with the FODD 560 may be achieved via the internet, or other means of wired or wireless communication. In certain embodiments, input source 502 communicates with either the cost matrix 570, the FODD 560, or both, over a computer network 540, according to any suitable connection, topology, scale or technology. In certain embodiments, the criterion matrix is automatically updated to reflect "learned" electricity consumption preferences, behaviors, rules, etc.

FIG. 5 further depicts an electricity meter 506, such as a smart meter, which may be coupled to a source of electricity 504, which provides electricity to the home 580 via, for example, above or below-ground power lines.

The home 580 depicted in FIG. 5 is an example end user that may be included within an energy management system in accordance with the embodiments disclosed herein. However, it should be understood that discussion of home 580 with reference to FIG. 5 may be applicable to other types of end users, such as, for example, factories, offices or other commercial buildings, or any other point of energy consumption or production. In certain embodiments, home 580 includes one or more electricity-consuming devices, such as, for example, electric or hybrid-electric vehicles 514, power strips 510 (e.g. "smart" power strips) or various household appliances (e.g., "smart" appliances 512). The home 580 may include a smart thermostat 516. In certain embodiments, the end user is equipped with one or more power generating devices or sources of renewable energy, such as devices that generate electricity from wind 590 or from solar energy 592 (i.e., photovoltaics), among possibly others. The home 580 may include a device for energy storage and/or generation 530. In certain embodiments device 530 includes an electrical storage battery. In certain embodiments, a user/consumer may have a generator for use during power outage or insufficient local power generation. An electrical storage unit may be useful for a number of reasons. For example, electricity may be cheaper to buy or sell at certain time periods, and therefore storage of electricity for use at certain time periods may be desirable. Moreover, power requirements may be greater during certain periods of time, and therefore storage of electricity for use during periods of greater need may be desirable. The following example, which is not intended to limit or define the scope of any terms or concepts disclosed herein, may be helpful in demonstrating the possible utility of an electrical storage device in a FODD-based electricity distribution system: In a certain embodiment, energy may be less expensive to buy or sell at 3:00 p.m. than it is at 5:00 p.m. In this particular example, it is assumed that at 5:30, energy storage is at around 70%. If a family usually comes home at around 6:00 p.m. and needs a significant amount of electricity at that time, an unsophisticated system may sell energy at 3:00 p.m. and buy it back at the more expensive rate at 6:00 p.m. A FODD system, however, may take energy usage patterns into account to reduce energy expenses of a user. For example, if a storage battery is charged prior to 5:00 p.m., electricity may possibly be sold at around 5:00 pm at a higher rate. At 6:00 p.m., when the family comes home, the FODD may make the decision to start drawing down the battery at 60% and buy electricity at 40%. In this way, the battery maybe still be 30% charged by the time the family goes to bed. Ideally, it would be almost at zero by the time the sun comes up and the user's photovoltaic panels start generating energy adequate to meet the user's energy requirements. The FODD algorithm in this case may be programmed into the FODD via a criterion matrix, or simply "learned" by the FODD using artificial intelligence.

The home 580 may include an internet connection device 542. In certain embodiments, end user 580 includes a programming and/or monitoring unit 520, which may be accessible through wired or wireless communication. For example, the unit 520 may be accessible externally via the internet, or through a control device local to the end user 580. The devices described above may communicate with the FODD, or each other, via a wireless or wired network.

Water Distribution System

There is an acute water shortage in many parts of the world. Population growth and the projected climate changes are likely to exacerbate these shortages. More sophisticated methods are needed to make certain that water is not wasted.

Similar to the electrical grid system, a Flow Optimizer Decision Device (FODD) may be used to optimize and coordinate water flow. For example, FODD may be used in large scale applications such as the water system for a particular state or country. It may also be used in a smaller scale for farms and even individual homes and businesses.

On a large scale, a FODD may be used to monitor reservoirs, dams, etc. and assist in water distribution. The criterion on how water is to be distributed may be complex, particularly during periods of drought. Therefore, how water is disseminated may depend on complex criterion matrices. These rules or criterions may even be legal in nature due to water rights. In addition to criterion requirements on reservoir management, in certain embodiments, a FODD receives information from weather forecast facilities or other sources such as the USGS National Water Information System;

USGS posts and disseminates real-time water conditions (surface, ground, and water quality). In addition to these information sources, a FODD may receive information from water quality sensors and make decisions as to shut the offending water supply down or dilute it with other sources to bring the levels to acceptable levels. These decisions may be governed by criterion matrices that are downloaded to the FODD.

Figure 6:
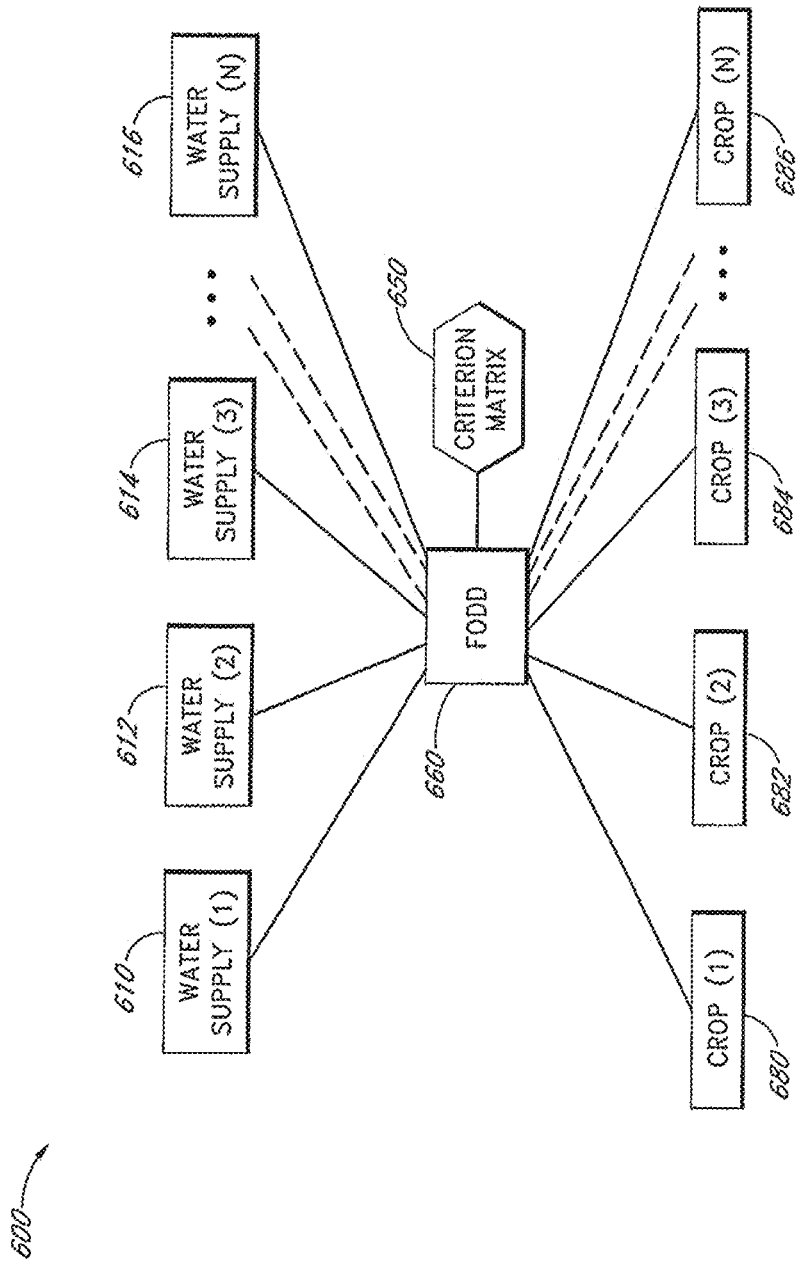
FIG. 6 illustrates an embodiment of a water management system.

On a smaller scale, a FODD can be used to make irrigation decisions. FIG. 6 illustrates a water management system 600 incorporating a FODD 660. In certain embodiments, the FODD 660 manages the distribution of water from one or more water supplies 610-616 to one or more crop regions 680-686, or other water consumption points. FODD 660 may determine how water from supply sources should be distributed based on information from one or more criterion matrices 650. Criterion matrices 650 may contain rules for irrigating various crops, wherein such rules relate to, for example, costs associated with water from one or more particular water sources, or other factors. In certain embodiments, a FODD criterion matrix 650 accounts for one or more parameters related to water distribution, such as weather forecast information, crop type, growing season, input from ground moisture sensors, etc. For example, based on the growing season and the type of crop, relative humidity, temperature, ground moisture, etc. The FODD 660 may direct a sprinkler system to discontinue irrigation or sub-irrigation prior to an expected rainfall. As another example, the FODD 660 may selectively irrigate moisture sensitive crops. In certain embodiments, the criterion matrix is automatically updated to reflect "learned" water consumption/distribution preferences, behaviors, rules, etc.

The following example is provided for illustrative purposes only, and does not limit or define the scope of any terms or concepts disclosed herein: In a certain embodiment a homeowner has a sprinkler system. During periods when rain is falling, the homeowner may wish to turn off the sprinkler system. A FODD may be configured to consider weather forecasts, soil moisture information, or other factors or parameters, and may cause the sprinkler system to be turned off, or recommend turning off the sprinkler system. In certain embodiments, the FODD may cause or recommend that certain zones or regions (discussed in further detail below). The FODD may cause reactivation under certain conditions as well. Such a FODD may be equipped with a default program for a particular area or vegetation profile. In certain embodiments, programming changes may be implemented via a computer, cell phone, or other media device.

In certain embodiments, the FODD 660 can handle different zones dynamically. For example, if zone A has plants that require a significant moisture and Zone B has fruit trees that require low moisture, a soil sensor may read the ground moisture of Zones A and/or B. This information, together with other information such as the weather forecast, may dictate on how to irrigate Zone A and/or B. Moreover, the system may be programmed concerning, or "learn," irrigation patterns conducive to healthy plant/crop growth over a period of time and/or for various seasons.

Medication Distribution System

Figure 13:
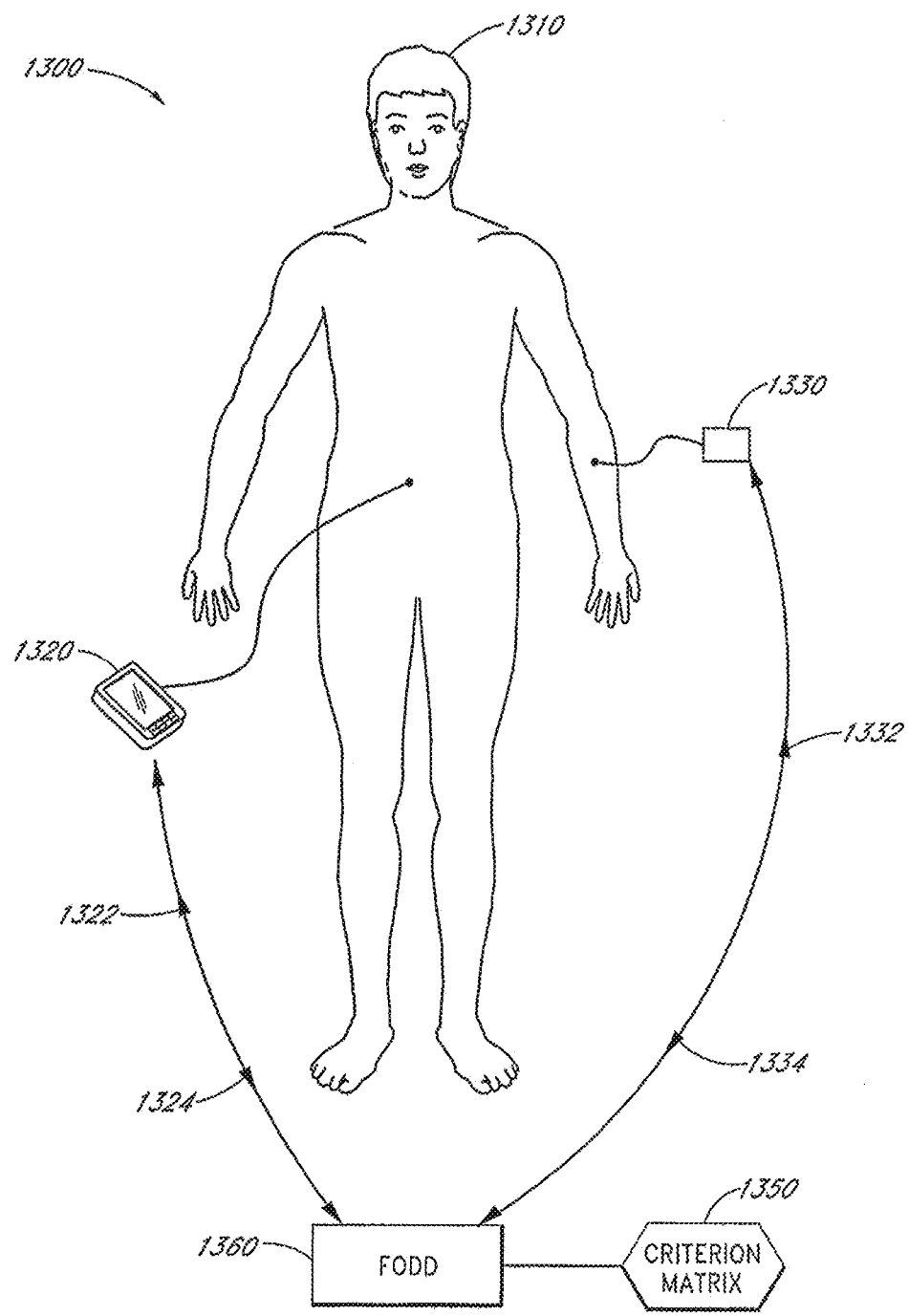
FIG. 13 illustrates an embodiment of a medication distribution management system.

A Flow Optimizer Decision Device (FODD) may be used to optimize and/or coordinate monitoring and delivery of medication to a patient. FIG. 13 illustrates an embodiment of a medication distribution system in the context of treatment of a diabetic patient 1310. However, references to diabetes-related monitoring and distribution are made solely to aid in the understanding of broader concepts discussed herein. It should, therefore, be understood that a FODD-based medication distribution system may be used for any suitable medication or medical intervention. For example, a FODD may be used in connection with the monitoring and delivery of chemotherapy medications, to assist in preventing the application of too much or too little medication and/or therapy.

With reference to FIG. 13, a monitoring device 1320 provides information relating to one or more physiological parameters of a patient 1310, such as blood glucose level. The system 1300 includes a FODD 1360 in communication with the monitoring device 1320 (e.g., a glucose monitoring device). Communication between the monitoring device 1320 and the FODD 1360 may be effected via a secure authentication system. In certain embodiments, information is uploaded from the monitoring device 1320 to the FODD via a secure authentication system. Information may be uploaded from the monitoring device 1320 to the FODD in real-time.

In certain embodiments, information provided by monitoring device 1320 may be used by the FODD 1360, in connection with a criterion matrix 1350 relating to medication adjustment, to perform, or cause to be performed, any or all of the following functions: Generate a report with suggestions or recommendations to a physician or other person or device relating to adjustment or maintenance of medication level. In certain embodiments, a physician may make adjustments, or provide authorization to make adjustment to medication levels. For example, once a physician approves adjustment or maintenance of medication level, such information may be communicated to a pharmacy or to the patient 1310. In the case of a wireless drug delivery implant system (e.g., an Insulin Release Device (IRD) 1330), medication may be automatically adjusted based on a preapproved matrix. In certain embodiments, medication adjustment or maintenance is authorized via a physician's secure electronic signature.

The information being transmitted may relate to one parameter or metric, such as blood glucose, or several, such as blood pressure, heart rate, etc. In certain embodiments, the FODD 1360 securely adjusts (or recommends adjustment of) medication levels with or without physician override. Medication levels may be checked against information relating to possible adverse side effects and/or interactions with other medications.

FODD 1360 may be used for adjusting medication in cases where a monitoring system is hard-wired into the patient 1310, at a hospital, residence, or other location. FODD 1360 may be local to the patient 1310, or may operate remotely.

What makes the FODD so unique is that for the first time, medications could be adjusted in real-time. In the case of the insulin example, the insulin would be released very close to how the natural body would react to rise in blood sugar, mimicking the patient's own pancreas. In certain embodiments, a FODD acts as an artificial pancreas, or other artificial organ. This has the potential to improve patient's lives and adherence to medication With further reference to FIG. 13, in certain embodiments, medication distribution device 1330 is an insulin releasing device. Such a device may be configured to receive commands (e.g. wireless communication via a network or through a device carried by the user such as a cell phone, or via a wired transmission, etc.) relating to adjustment or maintenance of insulin. In certain embodiments, device 1330 is configured to remove harmful substance from the body, either in addition to, or in place of, medication distribution functionality.

In certain embodiments, monitoring device 1320 is a glucose monitoring device. Such a device may measure blood glucose levels, possibly in addition to other parameters or metrics, such as blood pressure, heart rate, or other physiological parameters relating to the patient 1310. A glucose monitoring device may be an implanted device, and may obtain information relating to one or more physiological parameter in intervals, and transmit such information the FODD 1360. In certain embodiments, monitoring device 1320 is a measuring device that the patient 1310 can use to manually record information such as blood glucose or blood pressure, etc. The data may be transmitted directly by the device, through a wireless network, through an intermediary device such as a cell phone carried by the patient, or in any other suitable manner.

In certain embodiments, the FODD 1360 makes decisions with or without doctor or nurse approval override. Alternatively, it could make recommendations as to the correct course of action to be taken, such as an adjustment to medication delivery. Adjustment to the medication may be performed automatically (e.g., via the medication distribution device 1330) or prescription may be faxed/emailed/transmitted electronically to a pharmacy and/or patient. Feedback information from the medication delivery device 1330 may be transmitted 1334 to the FODD 1360. Such information may be helpful in confirming the actual amount or rate of insulin released to the patient 1310.

The FODD 1360 may transmit information 1332 to the insulin release device 1330 relating to the amount of insulin to be released. Such information transmission may be performed, for example, a) automatically by FODD 1360 via the criterion matrix 1350 or b) manually set by a physician via the FODD 1360, or c) a combination of (a) and (b) whereby the FODD 1360 may make a recommendation as to the amount of insulin to be released; the physician may then accept, reject or modify the recommended amount. In certain embodiments, information is transmitted or downloaded 1324 to the FODD 1360 from the glucose monitoring device 1320. Such information may include information relating to blood glucose and/or other parameters, such as heart rate, blood pressure, etc. In certain embodiments, the physician may instruct 1322 the FODD 1360 to add or remove parameters to or from the glucose monitoring device 1320. For example, in certain embodiments, if the physician desires to receive information relating to a particular parameter that the monitoring device 1320 is equipped to monitor, such as the amount of the actual insulin in the blood, such parameter may be added to the monitoring device 1320 and the criterion matrix 1350. In certain embodiments, the criterion matrix is automatically updated to reflect "learned" medication distribution or harmful substance removal preferences, behaviors, rules, etc.

Decisions made by the FODD 1360 may be made in any desired time increment (e.g., seconds, minutes, etc), or they may be made in real time. Decisions may be made with or without physician approval. In certain embodiments, the FODD 1360 bases decisions on the criterion matrix 1350. The criterion matrix 1350 may be made of individual functions, which take into account, for example, information such as blood glucose level, blood pressure, heart rate, etc. Moreover, the functions may include rules and/or limits on how medications should be adjusted based on the information received.

The FODD 1360 may be located remotely at any suitable location, at a physician's office, at the patient's residence, or may be a portable device, such as a device carried by, or implanted in, the patient 1310. In certain embodiments, one or more of the components 1320, 1330, 1360 and 1350 are incorporated into a single physical unit. The physical unit may be implanted into the patient as a single device.

The following example scenarios relating to the medication delivery system 1300 are discussed for explanation purposes only, and do not serve to limit or define terms used herein in any way. In a first example, a patient 1310 eats large meal, causing his or her blood glucose level to elevate. The glucose monitoring device may transmit information indicating the elevation in blood glucose level information to a FODD 1360. Based on a criterion matrix 1350 (the criteria of which may have been specified by a physician, or may be in accordance with certain medical guidelines), the FODD 1360 may adjust or cause to be adjusted the release of insulin to the patient 1310. This may be done by sending commands to an insulin release device 1330. The insulin release device may then release the appropriate amount of the insulin. In certain embodiments, this release of insulin is done without physician approval. In certain embodiments, physician approval or authorization is required. In certain embodiments, physician approval may be required in certain circumstances, while other circumstances do not require such approval. A report of activity relating to the monitoring and/or distribution of insulin (or other medication) may be logged or sent to a physician, or otherwise saved or transmitted.

In a second example, a patient 1310 eats large meal. However, the patient's blood glucose level does not elevate due to prior diet or exercise. A glucose monitoring device 1320 may transmit this information to a FODD 1360. Based on a criterion matrix 1350 (the criteria of which may have been specified by a physician, or may be in accordance with certain medical guidelines, etc.), the FODD 1360 may determine that no additional insulin is required. In certain embodiments the FODD 1360 may transmit such information to an insulin release device 1330, which, in turn, may fail to release additional insulin to the patient 1310.

In the two examples detailed above, the blood glucose monitoring device may be an implant. However, in certain embodiments, the monitoring device may be a unit that is not implanted, and may be manually operable by the patient, or another user. The information may be uploadable to the FODD 1360. Moreover, the medication release device 1330 may simply be a prescription or information that is sent to a patient or other person (e.g., via email or text) indicating how medication should be taken or adjusted.

Partner Cash Flow Analysis

A Flow Optimizer Decision Device (FODD) can be used to analyze very complex partnership structures in many industries such as real estate, the movie industry, the stock market, the insurance industry, banking, etc. A FODD may be used in any industry or scenario that requires investment with more than one person or entity. Moreover, a FODD may be used in situations involving a single investor.

With an advanced FODD algorithm, as described herein (see FIGS. 9-12 and corresponding discussion), one can analyze many complex investment scenarios automatically. In certain embodiments FODD algorithms are not limited by the number of investors, periods, or types of criterion requirements. A FODD algorithm, therefore, may help a partner decide on the best "deal structure" to maximize investment return and minimize risk, or otherwise achieve desired investment outcomes. Furthermore, as discussed above, FODD algorithms may be applicable to any system, method, or device relating to the regulation or management of flow, such as, for example, a Smart Power Strip, as discussed above.

Figure 7:
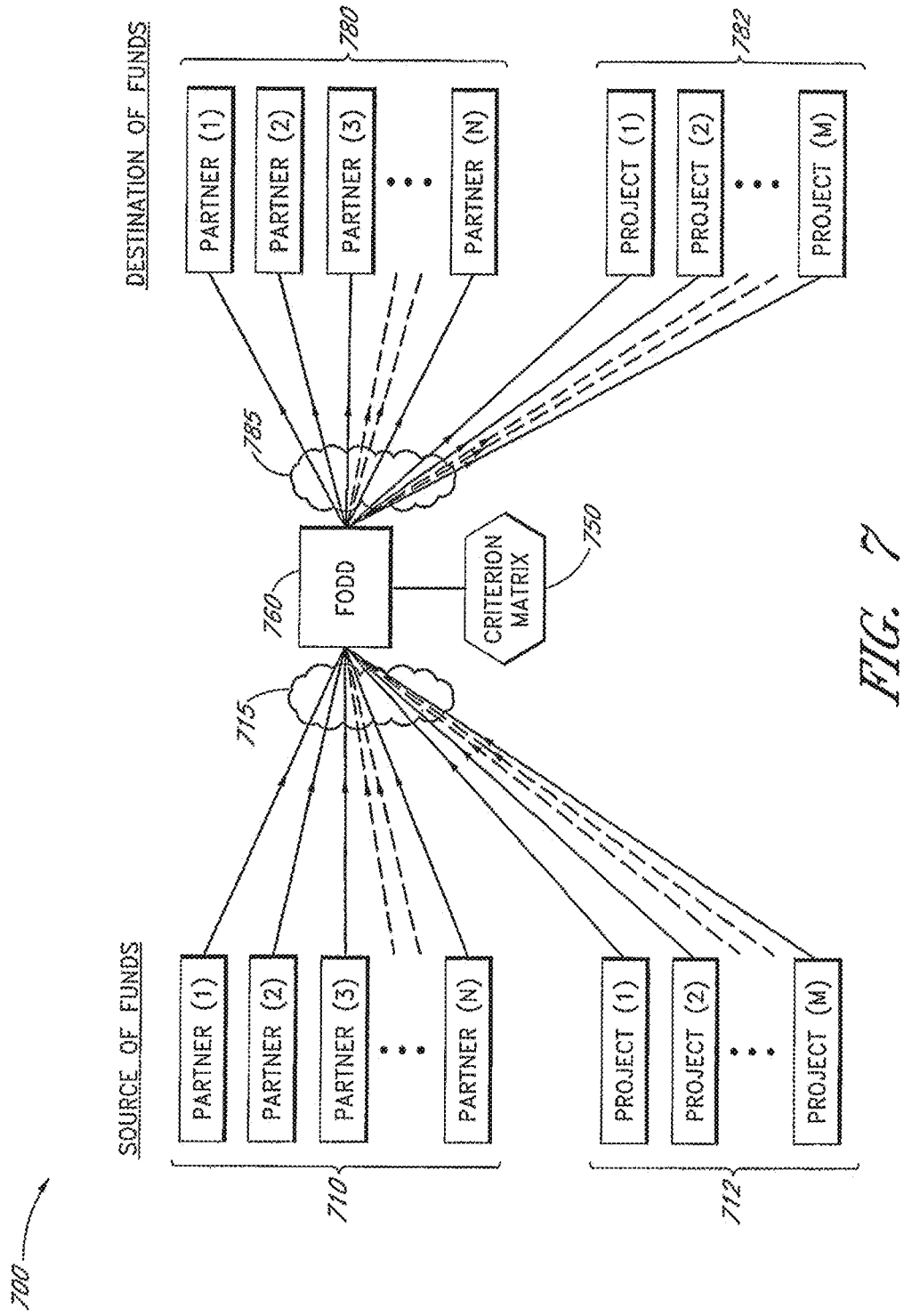
FIG. 7 illustrates an embodiment of a cash flow management system.

FIG. 7 illustrates an embodiment of a cash flow management system. For illustration purposes only, references are made herein to cash flow systems. However, it should be understood that embodiments and concepts disclosed herein are applicable any relevant type of flow. The system 700 may include one or more partners 710, 780 and/or one or more projects 712, 782. In FIG. 7, the total input of funds 715 in the system 700 is represented by the partner 710 and project 712 modules labels "Source of Funds." Initially project(s) 782 may need cash, and therefore the source of funds from projects 712 may be zero, or marginal; in such a case, the partners 710 may put up most or all of the cash. In later months, this dynamic may be reversed to some extent, whereby the partners 780 receive most of the cash and the project(s) 712 provide a substantial source of funds.

Figure 8:
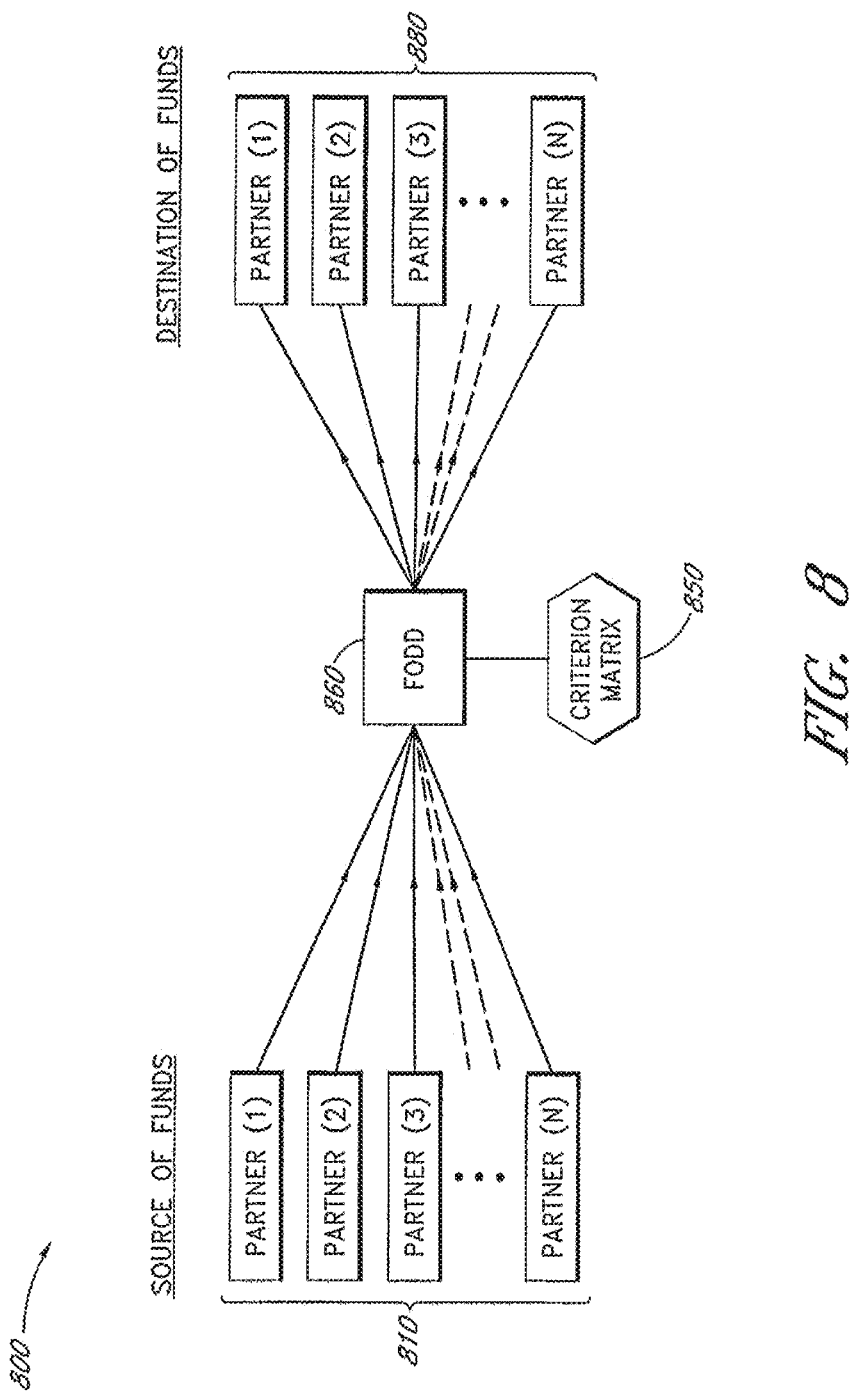
FIG. 8 illustrates an embodiment of a cash flow management system.
Figures 9, 9A, 9B:
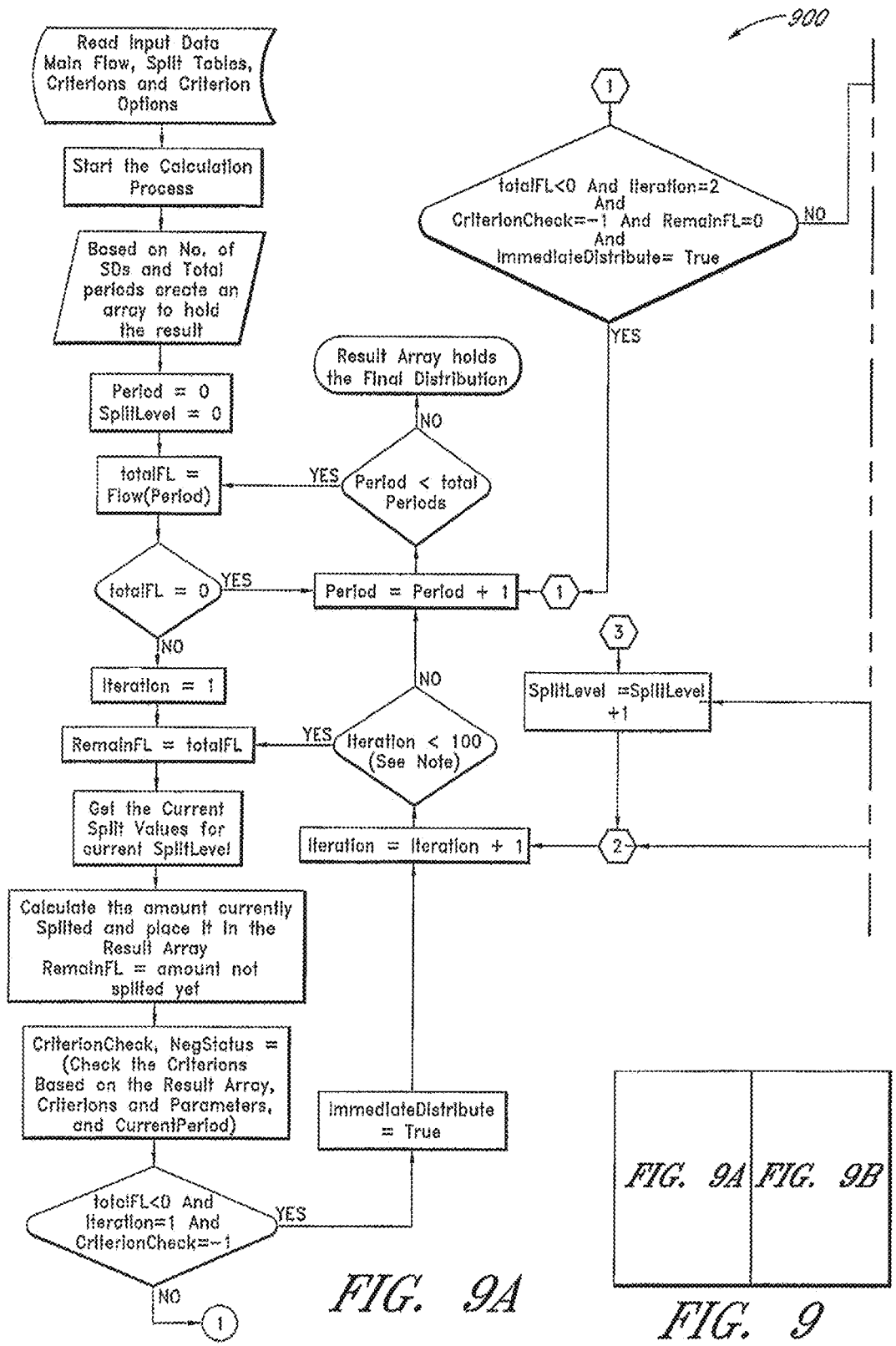
FIGS. 9 and 9A-9B illustrate an embodiment of a flow chart of a flow management system.
Figure 9B:
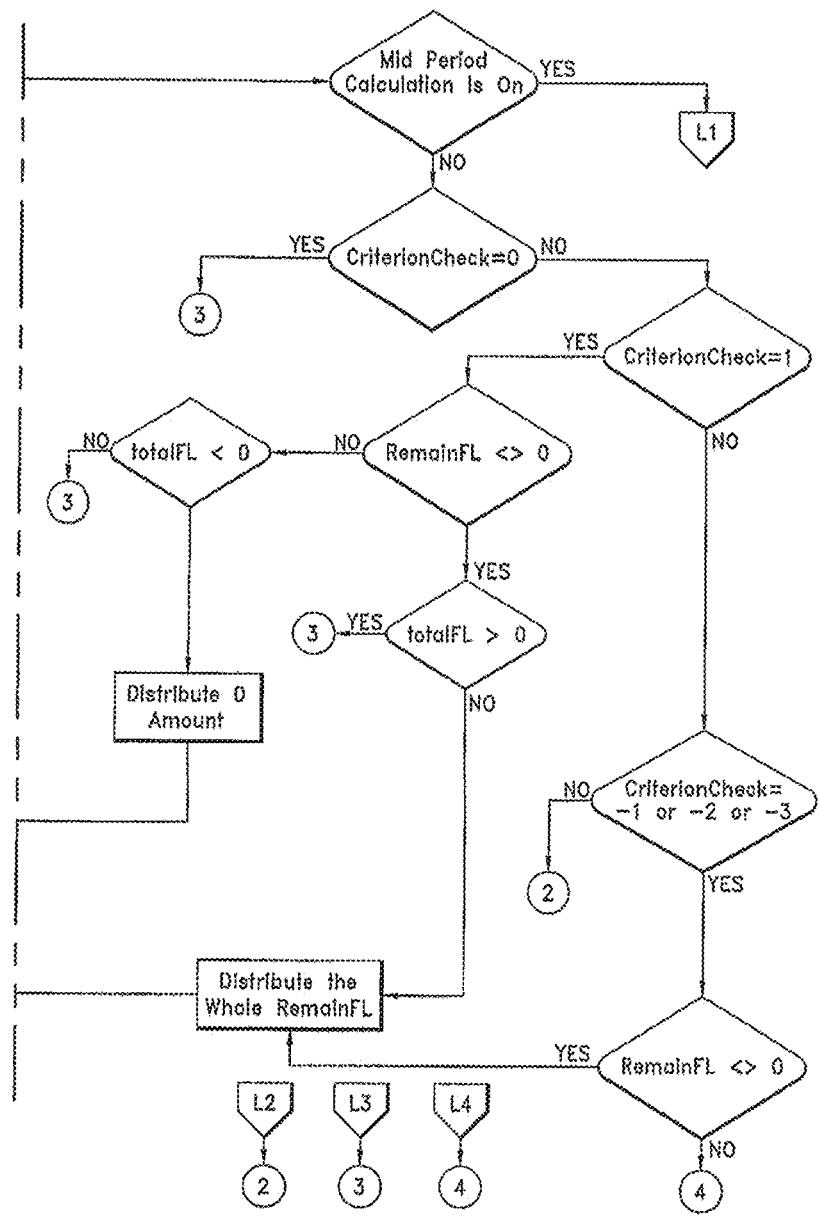
Figure 10:
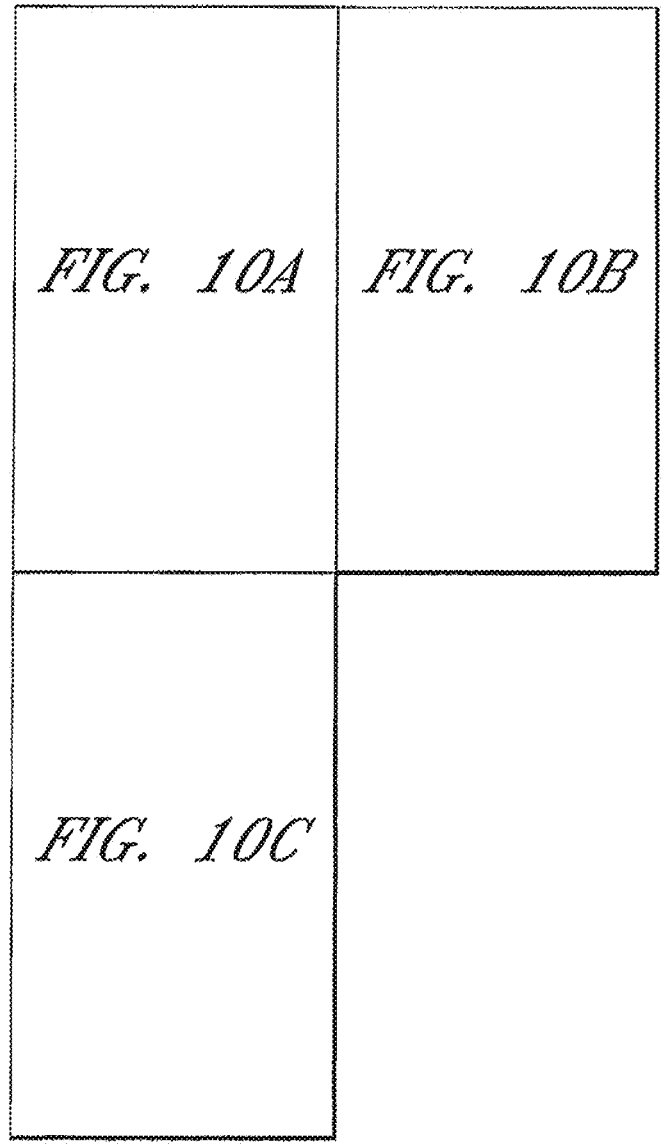
FIGS. 10 and 10A-10C illustrate an embodiment of a flow chart of a flow management system.
Figure 10A:
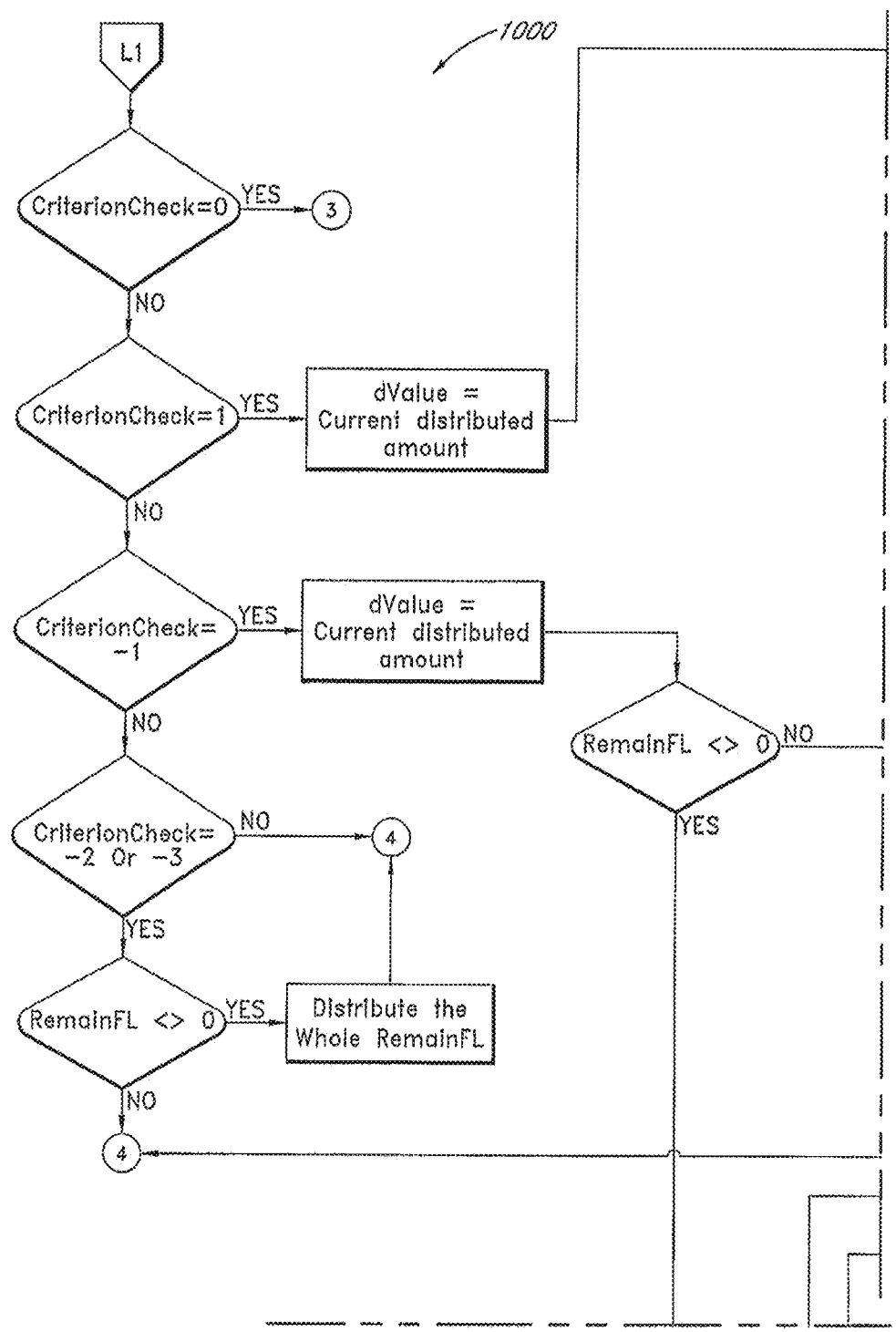
Figure 10B:
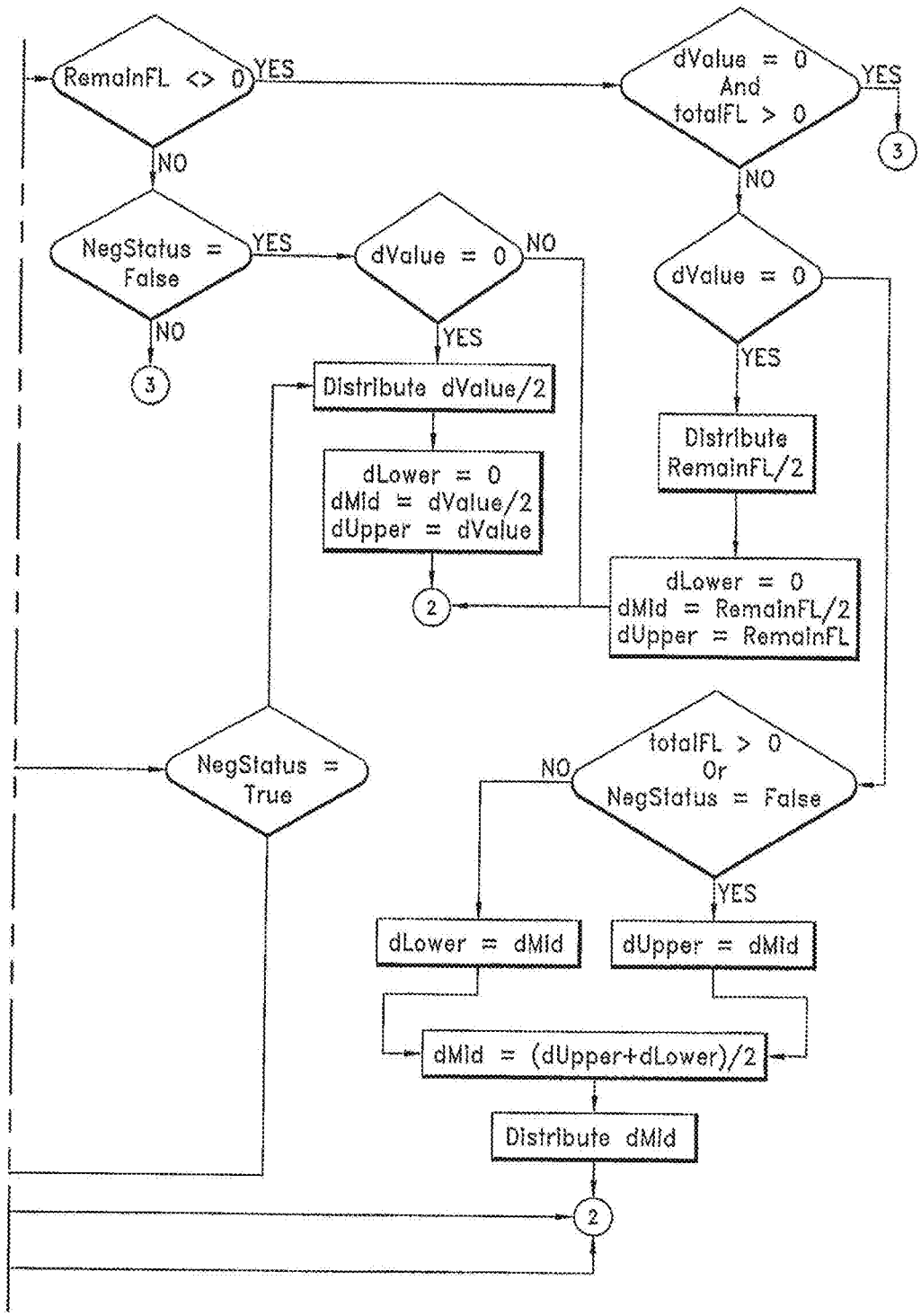
Figure 10C:
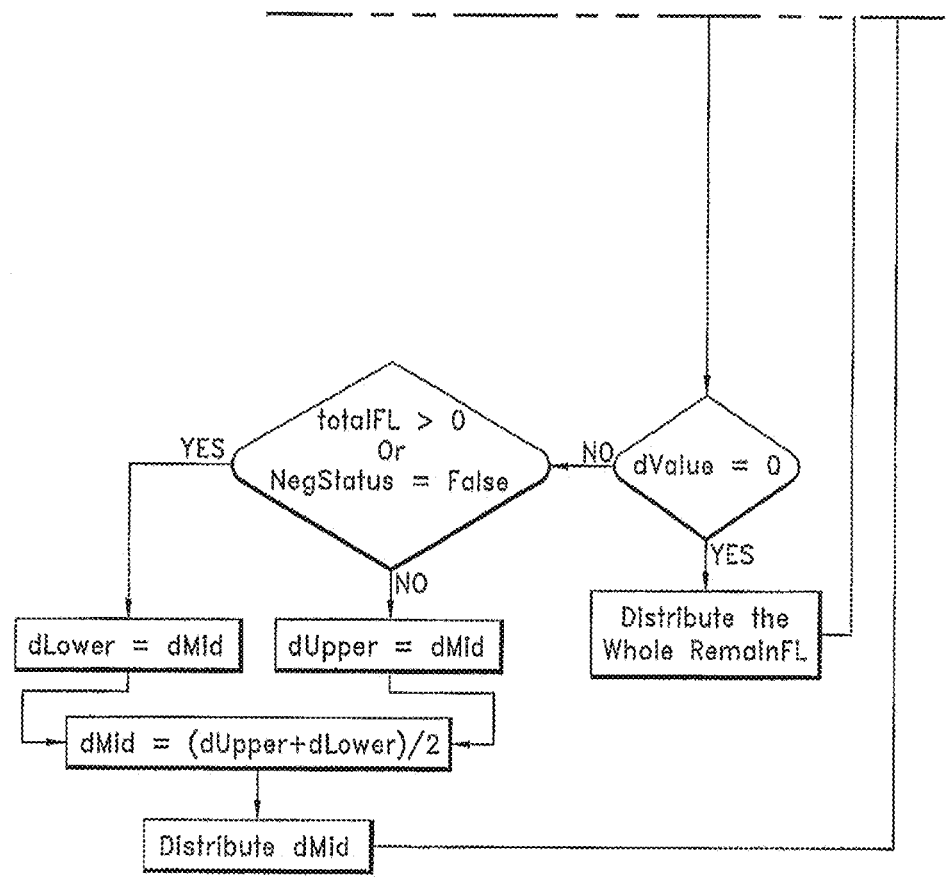
Figure 10C:
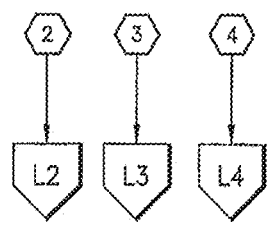
Figure 11:
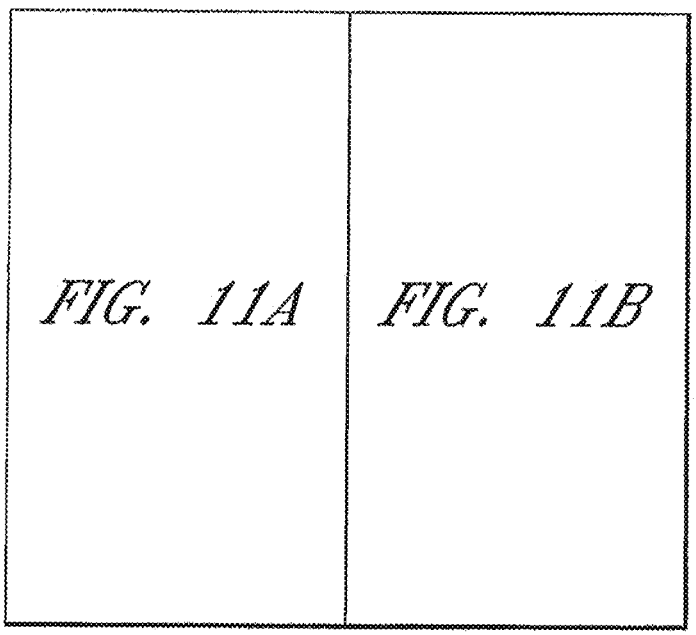
FIGS. 11 and 11A-11B illustrate an embodiment of a flow chart of a flow management system.
Figure 11A:
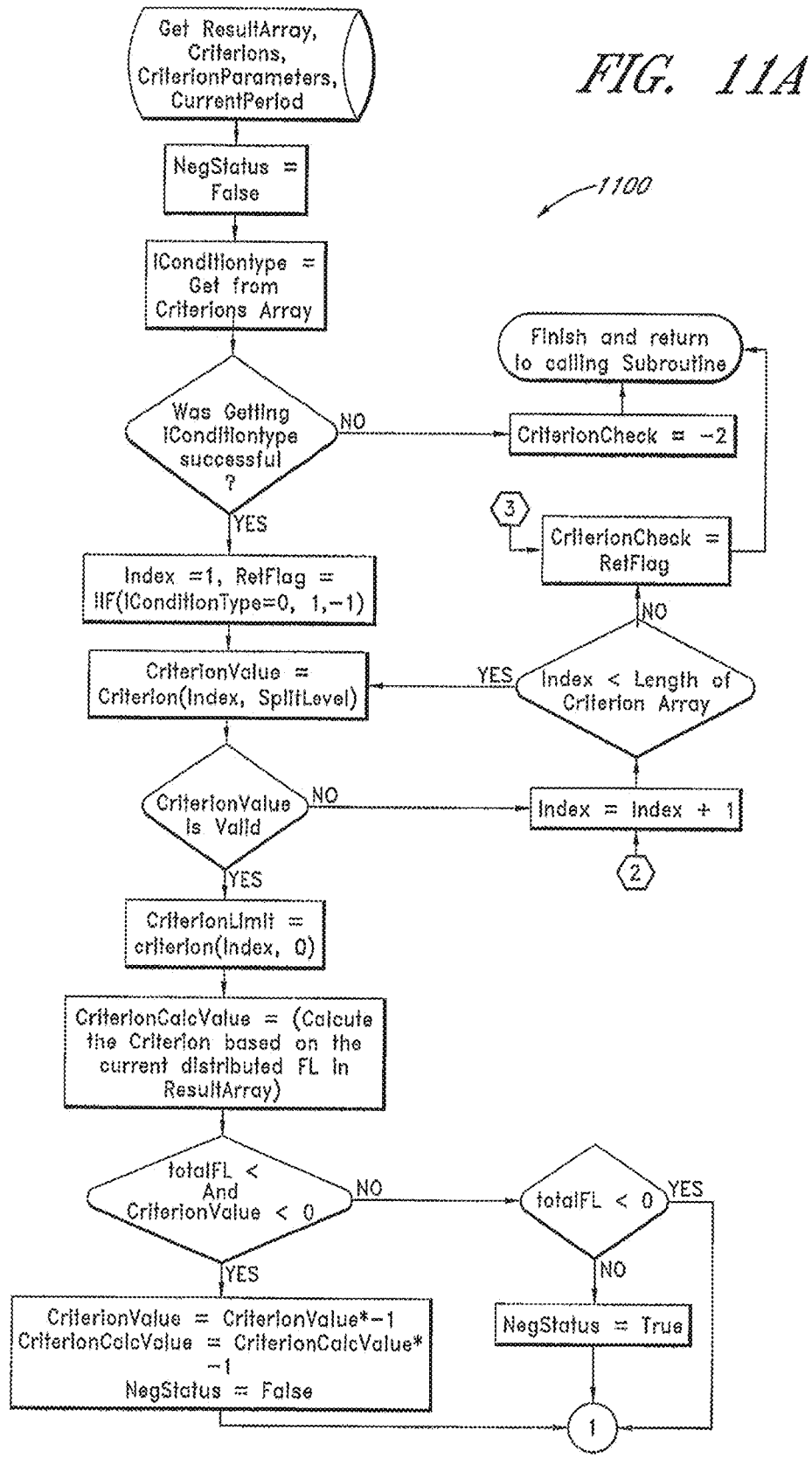
Figure 11B:
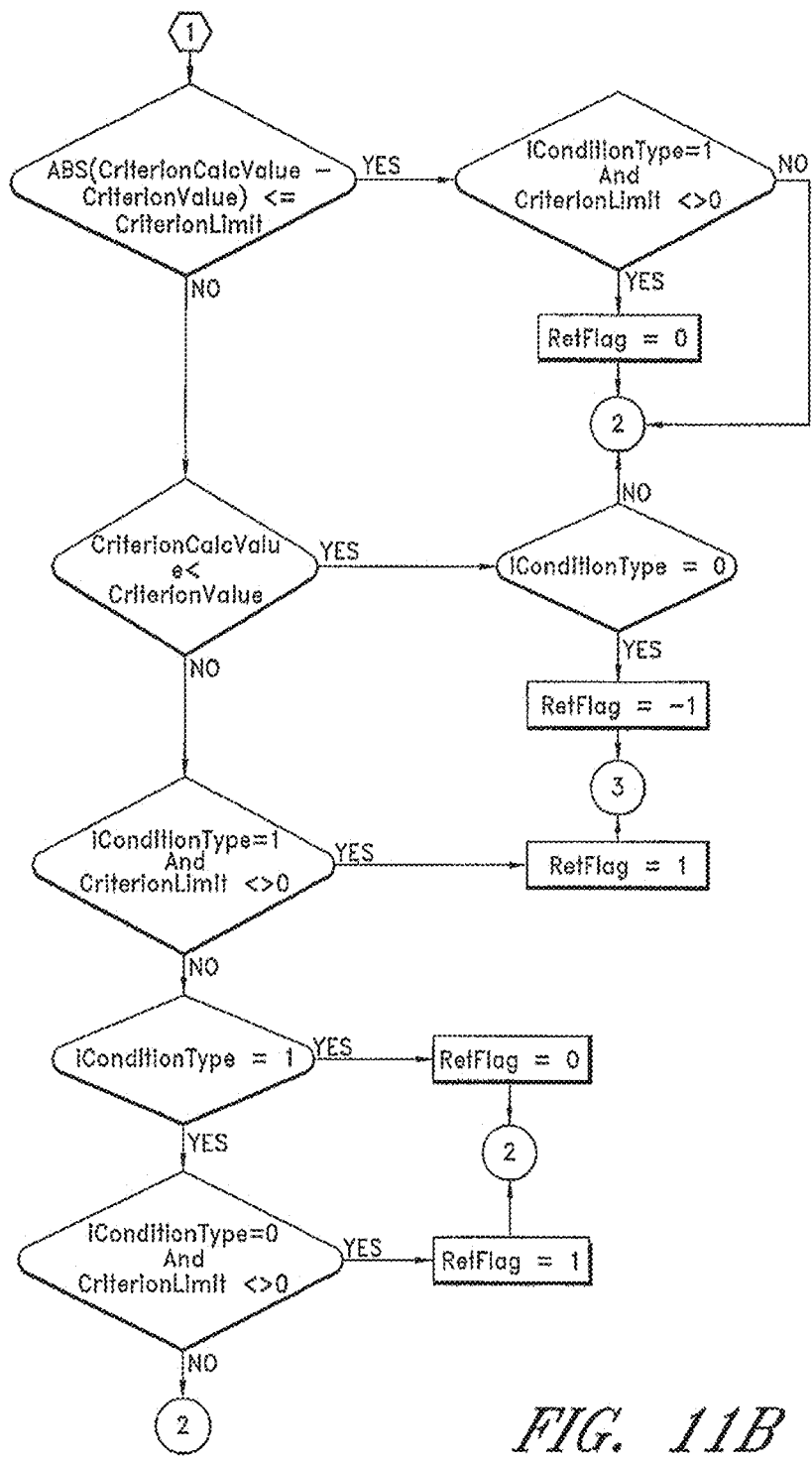

FIG. 8 provides a simplified representation of an embodiment of a cash flow management system, wherein net negative cash flows are considered sources of funds (i.e., investments) and net positive cash flows are considered uses of funds (i.e., returns). The terms "negative" and "positive" are used herein for illustration purposes only, and each of these terms may be subject to different meanings or understandings in certain systems, scenarios or circumstances. On examination, one can see that FIG. 8 shares some abstract structural similarity with the representation of a system for managing electricity flow depicted in FIG. 4.

Figure 12:
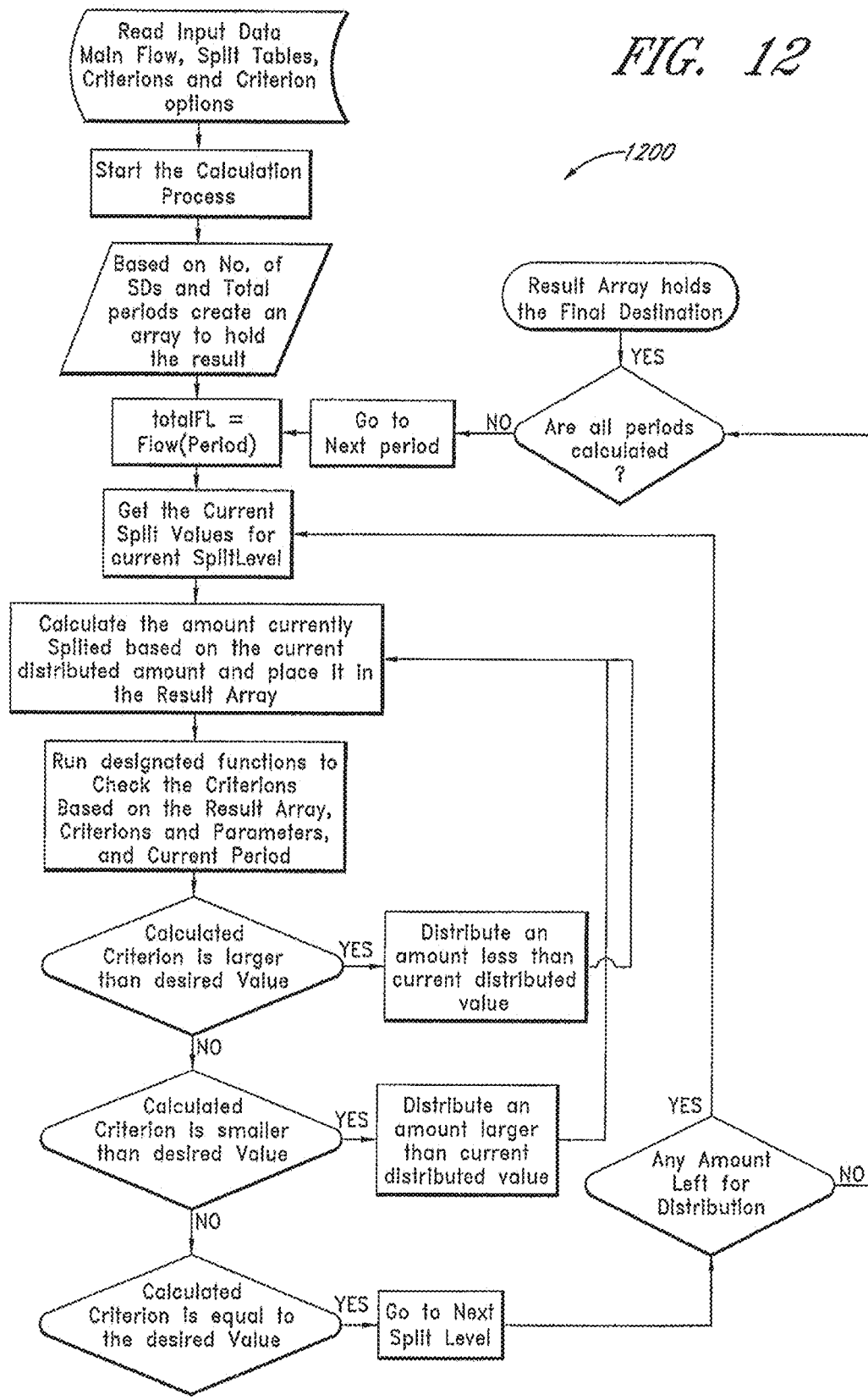
FIG. 12 illustrates an embodiment of a flow chart of a flow management system.

With respect to cash flow analysis, or any other flow regulation analysis, a FODD may use an algorithm similar to that depicted in FIGS. 9-12 to determine the percent distribution of each partner based on a criterion matrix 750, 850. FIGS. 9-12 illustrate flow charts representing a particular embodiment of an algorithm that may be used in association with certain embodiments of a FODD as described herein. FIG. 12 provides a summary of an example algorithm represented by FIGS. 9-11. The following notes provide explanation relating to the meaning of terms and variables used in the flow charts of FIGS. 9-12 and are provided solely to aid in the understanding of the flow charts, and in no way define or limit the terms or variables used therein:

Result Array: May begins with a zero values in the array and be filled during the process. When the process ends it contains the final result of the calculation Criterions: Milestones based on various targets calculated by various functions at each stage of the distribution. Once particular criterion hurdles are met, a flow chart may proceed to the next distribution in the sequence.

Functions: May be simple linear, non-linear or even very complex functions that require complex iterations to determine their values.

Parameter (Function Parameters): Parameters that describe the function, e.g., function name, constants in the function, etc.

Period: Indicates the period of calculation; when one period is finished, a flow chart may proceed to the next period. A period may be years, months, hours, seconds, millisecond, nanosecond, etc. A period may also be in real time, whereby samples are taken in real time and analyzed.

SplitLevel: SplitLevel 0 identifies the first set of criterions and split values. When one set of Criterion requirements are satisfied, a flow chart may proceed to the next SplitLevel and the next set of Criterions and SplitLevels will be used. Each split level may have its own sets of criterion matrix, unique function matrix, parameter matrix, etc.

Iteration: Iterate of calculating criterions and splits until the criterions converges. There may be a limit on the number of iterations. This may be a very large number. However, a number as small as 100 for the maximum iteration should suffice. Generally convergence occurs in 20-30 iterations.

CriterionCheck: Aids in determining the status of the current criterion calculation.

1—A value of 1 means that the calculated value is greater than the expected value.

2—A value of 0 means the calculation equals the expected value.

3—A value of −1 means that the calculated value is less than the expected value.

4—A Value of −2 means that there are no more criterion to calculate.

Negstatus: Flag that helps deal with negative flows. There may be total positive flows as well as total negative flows. In case of negative flows we can have unique/separate matrices for function, parameters, split levels, etc. Negative flows can be treated with different rules. This allows the Flow Optimizer Decision Device (FOOD) to analyze bi-directional flows.

iConditionType: There are two ways to check to see if the criterion is met: (1) ALL the conditions must be met, in this case iContitionType=O. Alternatively, (2) only one of the conditions must be met, in this case iConditionType=1. In summary, if all the conditions much be met (e.g.

Condition 1 AND Condition 2, And . . . ), then iConditionType=O; if any condition will do (e.g. Condition 1 OR Condition 2, OR, . . . ), then iConditionType=1.

In cases where both AND and OR are used (e.g. Condition 1 AND Condition 2 OR Condition 3 etc.), use of additional split levels may help accomplish this.

SD: Source or Destination of the Flow. When a flow is generated, it is from the source. The flow output/result is the Destination. The sum of all the Source of the Flow should equal the sum of all the Destinations of the flow. Some or all of the Source of the Flow may be the same as the destination of the Flow. In this way a Source may be the same as a destination. One Source of the flow may be zero and receive most of the flow (Destination) or it could be the majority of the source of the flow and receive little or nothing. The flow may be positive or negative.

As discussed above, the FODD can be used in many scenarios, such as, for example, electrical distribution systems. For illustration purposes only, some of the discussion herein relates specifically to real estate development. The following example may be helpful in demonstrating the implementation of such a FODD/algorithm: Assume a real estate development project with three partners, each being associated with his or her own risk aversion utility curve. In this example, Partner A may be very risk averse, Partner B may be less risk averse than Partner A, and Partner C may not contribute much cash and may instead be charged with the development of the project. As a developer, Partner C may be willing to take more risk as well.

The following example characteristics or rules may be included in a criterion matrix associated with a FODD suitable for regulation of cash flow between and among Partners A, B and C:

distribute 90% of the initial positive cash flow to partner A, 10% of the initial positive cash flow to partner B, and 0% to the developer (partner C) UNTIL THE FOLLOWING CONDITIONS ARE SATISFIED:
  i) Partner A gets all of initial investment back AND ii) Partner A gets a 4% Internal Rate of Return (IRR) on his money OR he gets a Net Present Value (NPV) equal to 120% of his initial investment at a 6% discount rate.
Once the above criterion are satisfied, then distribute 10% to partner A, 50% to partner B, and 40% to partner C (Developer) UNTIL THE FOLLOWING CONDITIONS ARE SATISFIED: i) Partner B gets 60% of his initial investment back AND a 12% IRR AND ii) Partner C (Developer) gets back 50% of his developer's fee (some predetermined amount perhaps) AND iii) Partner A not only gets all his money back (as dictated in the previous step) but he also gets a 12% IRR.
Once the above conditions are satisfied, distribute the cash flows equally between Partner B and C (Developer) until the sale/disposition of the property (the disposition would have its own criterion matrix similar to the above).

The above example may also be much more complex. More complex matrices may have many more steps with complex AND/OR Boolean logic. Moreover, negative cash flow may likewise require separate handling. The following issues may arise: If there were negative cash flows (project is losing money) who would put up the shortfall? In our example above, perhaps the developer (Partner C) or Partner B would put up the funds. The FODD 760, 860 may handle negative cash flow situations by including a separate negative flow criterion matrix. In this way, a FODD may be able to handle bi-directional flow, having separate rules for negative flows. This negative criterion matrix may be part of a main criterion matrix 750, 850.

The FODD 750, 850 may analyze the example scenario discussed above, and distribute cash flow for the particular period. Another unique feature of the FODD is that it may be capable of handling both of the following scenarios: 1) Full-period distributions as well as 2) mid-period distribution.

If, for example, the period unit under consideration is months, for a full-period distribution, the percent distribution would not be changed until the following month. In our example above, a criterion hurdle could be reached in the first week of the month (period). However, in this example, the percentage distribution would not change until the next month for a full-period distribution.

For a mid-period distribution, the FODD may provide an exact analysis. With reference to the example above, once the criterions (such as IRR, etc.) reach an exact figure (within tolerance parameter in the criterion matrix), then the FODD may proceed to the next level of distribution. Such FODD embodiments may be very accurate, since an IRR hurdle, for example, could be reached in the 3rd day of a particular month.

More Complex Situations and Sensitivity Analysis

It may also be desirable to analyze various cash flow scenarios with different partner structures. It may, therefore, be desirable to analyze various cash flow scenarios (e.g., cash flow scenarios 1, 2, 3, etc.) with various partners (e.g., Partners A, B, C, etc.), each being associated with a complex criterion matrix. In certain embodiments, a FODD may be used multiple times, using different criterion matrix inputs for each deal structure, to find an optimal solution.

FODD Used in a Partner Cash Flow Analysis Situation—Business Model

In case of use in partner cash flow analysis, a FODD may be used as a subscription service over the internet. For example, it may be used in any industry where some kind of partnership is desirable. Such industries include, but are not limited to:

Real Estate Transactions, Development, Brokerage
Advertising
Transportation
Oil, Gas, mining
Agriculture
Entertainment, Hollywood
Medical, Hospitals, Pharmaceuticals
Insurance Industry
Internet, E-Commerce, computer manufacturing, software
Communication such as telecom and wireless telecommunication
Manufacturing
Automotive
Construction
Utility companies and Energy ventures
Financial services where partners are involved such as banking
Food industry A specific website may be developed for each of the target industries. However, in each case, a FODD engine might be used to calculate the partner cash flow analysis.

There are at least four ways this business model may generate revenue:
1. As a subscription service. People/companies would pay to use it.
2. Sell advertisement targeted for the particular industry and audience.
3. Sell products or services for the targeted audience.
4. Put people together (collaboration) who are interested in a particular investment vehicle and collect a fee.

For example, a website might facilitate management of funds for partners or service providers who are interested in investing in a particular industry and/or in a certain geographical region. If a land owner wishes to sell his property, he might put his property up on a website. He could answer some questions on the website—thereby establishing a preliminary criterion requirement.

Another example may involve an apartment developer who wishes to use a website to input his cash flow requirements and a rough construction estimate. A general contractor who wishes to build the project and put his fee as an investment might also use the site to put a more detailed construction estimate. Investors and/or partners may also use the website to input their requirements on the project.

The various illustrative logical blocks, modules, and processes described herein may be implemented as electronic hardware, computer software, or combinations of both. To clearly illustrate this interchangeability of hardware and software, various illustrative components, blocks, modules, and states have been described above generally in terms of their functionality. However, while the various modules are illustrated separately, they may share some or all of the same underlying logic or code. Certain of the logical blocks, modules, and processes described herein may instead be implemented monolithically.

The various illustrative logical blocks, modules, and processes described herein may be implemented or performed by a machine, such as a computer, a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor, a controller, microcontroller, state machine, combinations of the same, or the like. A processor may also be implemented as a combination of computing devices, e.g., a combination of a DSP and a microprocessor, a plurality of microprocessors or processor cores, one or more graphics or stream processors, one or more microprocessors in conjunction with a DSP, or any other such configuration.

The blocks or states of the processes described herein may be embodied directly in hardware, in a software module executed by a processor, or in a combination of the two. For example, each of the processes described above may also be embodied in, and fully automated by, software modules executed by one or more machines such as computers or computer processors. A module may reside in a computer-readable storage medium such as RAM memory, flash memory, ROM memory, EPROM memory, EEPROM memory, registers, hard disk, a removable disk, a CD-ROM, memory capable of storing firmware, or any other form of computer-readable storage medium known in the art. An exemplary computer-readable storage medium can be coupled to a processor such that the processor can read information from, and write information to, the computer-readable storage medium. In the alternative, the computer-readable storage medium may be integral to the processor. The processor and the computer-readable storage medium may reside in an ASIC.

Depending on the embodiment, certain acts, events, or functions of any of the processes or algorithms described herein can be performed in a different sequence, may be added, merged, or left out all together. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the disclosure describes, and points out novel features as applied to various embodiments, it will be understood that various omissions, substitutions, and changes in the form and details of the logical blocks, modules, and processes illustrated may be made without departing from the spirit of the disclosure. As will be recognized, certain embodiments of the inventions described herein may be embodied within a form that does not provide all of the features and benefits set forth herein, as some features may be used or practiced separately from others.

What is claimed is:

1. A power strip comprising:
    an electrical plug associated with the power strip, the electrical plug configured to be plugged into an external electrical socket to obtain power from a utility;
    at least a first electrical socket on the power strip, the first electrical socket configured to be electrically coupled to an energy storage and generation device that generates and stores electricity from one or more renewable energy sources;
    at least a second electrical socket on the power strip, the second electrical socket configured to be electrically coupled an energy consumption device;
    wireless communications circuitry within the power strip for obtaining utility cost information;
    a flow optimizer decision device within the power strip configured to direct transmission of electricity from the electrical plug to the energy storage and generation device via the first electrical socket to store electricity in the energy storage and generation device based at least in part on when the utility cost information is below a cost threshold and based at least in part on when energy capacity of the energy storage and generation device is below full capacity; and
    the flow optimizer decision device further configured to direct transmission of electricity from the energy storage and generation device via the first electrical socket to the second electrical socket coupled to the energy consumption device based at least in part on when the utility cost information is above the cost threshold and based at least in part on when the energy storage and generation device is above a storage threshold.

2. The power strip of claim 1, wherein the utility cost information comprises electricity rate information.

3. The power strip of claim 1, wherein the flow optimizer decision device is further configured to direct transmission of electricity from the energy storage and generation device via the first electrical socket to the second electrical socket coupled to the energy consumption device based at least in part on personal preferences of a user.

4. The power strip of claim 1, wherein the flow optimizer decision device is further configured to direct transmission of electricity from the energy storage and generation device via the first electrical socket to the second electrical socket coupled to the energy consumption device based at least in part on energy demands of the energy consumption device.

5. The power strip of claim 1, wherein the flow optimizer decision device is further configured to direct transmission of electricity from the energy storage and generation device via the first electrical socket to the second electrical socket coupled to the energy consumption device based at least in part on time of day and/or day of week information.

6. The power strip of claim 1, wherein the flow optimizer decision device is further configured to receive information from a smart meter and to control flow of electricity among the electrical plug, the first electrical socket and the second electrical socket based on the information.

7. The power strip of claim 1, wherein the flow optimizer decision device is further configured to receive feedback information from the energy consumption device and to control flow of electricity from the first electrical socket to the second electrical socket based on the feedback information.

8. The power strip of claim 1, wherein the flow optimizer decision device is further configured to receive information from a smart grid electrical system.

9. The power strip of claim 8, wherein flow optimizer decision device disables electricity provided from the electrical plug to the second electrical socket when the utility cost information is above the cost threshold.

10. The power strip of claim 1, wherein the flow optimizer decision device is programmable by a user.

11. The power strip of claim 1, wherein the flow optimizer decision device determines learned parameters based on electricity usage practices of a user.

12. The power strip of claim 11, wherein the flow optimizer decision device controls when to transfer electricity from the electrical plug to the first electrical socket to store electricity in the energy storage and generation device based at least in part on the learned parameters.

13. The power strip of claim 11, wherein the flow optimizer decision device controls when to transfer electricity from the first electrical socket to the second electrical socket to provide electricity from the energy storage and generation device to the energy consumption device based at least in part on the learned parameters.

14. The power strip of claim 11, wherein the flow optimizer decision device determines the learned parameters without user input.

15. The power strip of claim 14, wherein the flow optimizer decision device disables the electricity provided to the second electrical socket based on the learned parameters.

16. The power strip of claim 14, wherein the flow optimizer decision device continues to direct transmission of electricity from the electrical plug to the second electrical socket when the utility cost information is above the cost threshold if the energy consumption device is medical equipment.

17. The power strip of claim 1, wherein the flow optimizer decision device disables electricity provided to the second electrical socket when an amount of electricity consumed the energy consumption device exceeds a threshold.

18. The power strip of claim 1 further comprising a third electrical socket on the power strip connected to another power consumption device, the flow optimizer decision device configured to direct transmission of electricity to the second and third electrical sockets based on priority of the power consumption devices.

19. The power strip of claim 1 further comprising a third electrical socket on the power strip connected to another power consumption device and wherein the flow optimizer decision device is configured to direct transmission of electricity the first electrical socket to the second electrical socket, and simultaneously direct transmission of electricity from the electrical plug to the third electrical socket based on user criteria.

20. The power strip of claim 1 further comprising one or more lighted indicators that indicate cost of electricity consumption.

* * * * *